United States Patent
Kawano et al.

(10) Patent No.: US 9,433,632 B2
(45) Date of Patent: Sep. 6, 2016

(54) DRY COATED TABLET

(71) Applicant: Takeda Pharmaceutical Company Limited, Osaka-shi, Osaka (JP)

(72) Inventors: Tetsuya Kawano, Osaka (JP); Yasushi Mima, Osaka (JP); Yumiko Ishii, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/361,554

(22) PCT Filed: Nov. 29, 2012

(86) PCT No.: PCT/JP2012/081583
§ 371 (c)(1),
(2) Date: May 29, 2014

(87) PCT Pub. No.: WO2013/081177
PCT Pub. Date: Jun. 6, 2013

(65) Prior Publication Data
US 2014/0335181 A1   Nov. 13, 2014

(30) Foreign Application Priority Data
Nov. 30, 2011   (JP) .................................. 2011-262679

(51) Int. Cl.
| | |
|---|---|
| *A61K 9/16* | (2006.01) |
| *A61K 9/28* | (2006.01) |
| *A61K 9/32* | (2006.01) |
| *A01N 43/00* | (2006.01) |

(Continued)

(52) U.S. Cl.
CPC ............. *A61K 31/616* (2013.01); *A61K 9/209* (2013.01); *A61K 9/2054* (2013.01); *A61K 9/2095* (2013.01); *A61K 9/2846* (2013.01); *A61K 9/2886* (2013.01); *A61K 9/5078* (2013.01); *A61K 31/4439* (2013.01); *A61K 45/06* (2013.01); *A61K 9/5026* (2013.01)

(58) Field of Classification Search
None
See application file for complete search history.

(56) References Cited

U.S. PATENT DOCUMENTS

| | | | |
|---|---|---|---|
| 6,235,311 B1 | 5/2001 | Ullah et al. | |
| 6,328,994 B1 * | 12/2001 | Shimizu | ............... A61K 9/0056 424/464 |

(Continued)

FOREIGN PATENT DOCUMENTS

| | | |
|---|---|---|
| CA | 2 624 513 | 4/2007 |
| JP | H04-346930 | 12/1992 |

(Continued)

OTHER PUBLICATIONS

"Bayaspirin tablet 100 mg", Bayer, 2008.

(Continued)

*Primary Examiner* — Jeffrey T Palenik
(74) *Attorney, Agent, or Firm* — Hamre, Schumann, Mueller & Larson, P.C.

(57) ABSTRACT

Provided is a dry coated tablet showing high stability of the active ingredient (proton pump inhibitor, acetylsalicylic acid), which stably and rapidly expresses the pharmacological effect of the active ingredient after administration. A dry coated tablet having an inner core and an outer layer, wherein the inner core is an enteric-coated tablet containing acetylsalicylic acid, and the outer layer contains enteric micro granules containing a proton pump inhibitor.

3 Claims, 4 Drawing Sheets

(51) Int. Cl.
*A61K 31/616* (2006.01)
*A61K 9/24* (2006.01)
*A61K 31/4439* (2006.01)
*A61K 45/06* (2006.01)
*A61K 9/20* (2006.01)
*A61K 9/50* (2006.01)

(56) References Cited

U.S. PATENT DOCUMENTS

| | | | |
|---|---|---|---|
| 6,926,907 B2 * | 8/2005 | Plachetka | A61K 9/209 424/457 |
| 8,114,435 B2 * | 2/2012 | Depui | A61K 9/2081 424/451 |
| 2005/0249811 A1 * | 11/2005 | Plachetka | A61K 9/1611 424/472 |
| 2007/0122470 A1 | 5/2007 | Johansson et al. | |
| 2008/0166407 A1 | 7/2008 | Shalaby et al. | |
| 2013/0243859 A1 * | 9/2013 | Mima | A61K 31/4439 424/465 |

FOREIGN PATENT DOCUMENTS

| | | |
|---|---|---|
| JP | 2009-510139 | 3/2009 |
| JP | 2010-59119 | 3/2010 |
| WO | WO 97/25064 | 7/1997 |
| WO | WO 99/59544 | 11/1999 |
| WO | WO 00/06126 | 2/2000 |
| WO | WO 02/098352 | 12/2002 |
| WO | WO 2005/076987 | 8/2005 |
| WO | WO 2007/064274 | 6/2007 |
| WO | 2010/151697 | 12/2010 |
| WO | WO 2011/144994 | 11/2011 |

OTHER PUBLICATIONS

Lehman et al., "Fast Disintegrating Controlled release Tablets from Coated Particles", Drugs made in Germany 37, No. 2, 1994, pp. 53-60.

Office Action issued in corresponding Japanese Application No. 2014-525239, Jan. 12, 2016, 6 pages with an English translation.

* cited by examiner

DRY COATED TABLET

TECHNICAL FIELD OF THE INVENTION

The present invention relates to a dry coated tablet containing a proton pump inhibitor (hereinafter sometimes to be referred to as PPI) and acetylsalicylic acid. More particularly, the present invention relates to a dry coated tablet which is superior in the stability of the active ingredient and expresses a pharmacological effect stably and rapidly after administration.

BACKGROUND OF THE INVENTION

It sometimes happens that low dose acetylsalicylic acid administered to suppress thrombus and/or embolization (antiplatelet therapy) in cerebrovascular and circulatory diseases induces gastric ulcer or duodenal ulcer. Since discontinuation of administration of acetylsalicylic acid may result in thrombus and/or embolization, it is considered important to continue administration of low dose acetylsalicylic acid while suppressing the onset of ulcer.

While acetylsalicylic acid is also known as a non-steroidal anti-inflammatory drug (NSAIDs), and mainly used for the treatment of pain, fever and inflammation, non-steroidal anti-inflammatory drug may cause gastric ulcer or duodenal ulcer. Particularly, in the treatment of rheumatoid arthritis, osteoarthritis and the like, discontinuation of administration of non-steroidal anti-inflammatory drug may be difficult, since it markedly degrades the quality of life (QOL). Therefore, it is considered important to continue administration of non-steroidal anti-inflammatory drug while suppressing the onset of ulcer.

On the other hand, since PPIs of benzimidazole compounds (e.g., lansoprazole, omeprazole and the like) have a strong gastric acid secretion-inhibitory action, a gastric mucosa-protective action and the like, they have been widely used as therapeutic agents for peptic ulcer and the like. Particularly, lansoprazole preparation has obtained an approval also in Japan in recent years on the efficacy of "suppression of onset of gastric ulcer or duodenal ulcer by administration of low dose acetylsalicylic acid" and "suppression of onset of gastric ulcer or duodenal ulcer by administration of non-steroidal anti-inflammatory drug", and a clinical effect of suppression of the onset of gastric ulcer or duodenal ulcer due to the dosing of acetylsalicylic acid has been demonstrated.

Patent document 1 (WO 97/25064) discloses an oral pharmaceutical dosage form for oral administration, which contains an acid susceptible proton pump inhibitor with at least one kind of non-steroidal anti-inflammatory drug and, when desired, a pharmaceutically acceptable diluent.

Patent document 2 (WO 2007/064274) discloses an oral pharmaceutical dosage form comprising, as active ingredients, an acid susceptible proton pump inhibitor together with acetyl salicylic acid or a derivative thereof and optionally pharmaceutically acceptable diluents, characterized in that the dosage form is in the form of an oral fixed combination dosage form comprising a group of separate physical units comprising the acid susceptible proton pump inhibitor and one or more other separate physical units comprising the acetyl salicylic acid or a derivative thereof, and wherein at least the proton pump inhibitor is protected by an enteric coating layer.

Patent document 3 (WO 2005/076987) discloses a pharmaceutical composition comprising: (a) a therapeutically effective amount of at least one acid labile proton pump inhibitor; (b) at least one buffering agent in an amount sufficient to increase gastric fluid pH to a pH that prevents acid degradation of at least some of the proton pump inhibitor in the gastric fluid; and (c) a therapeutically effective amount of at least one non-steroidal anti-inflammatory drug.

Patent document 4 (WO 2002/098352) discloses a pharmaceutical composition in unit dose form suitable for oral administration to a patient, comprising: (a) an acid inhibitor present in an amount effective to raise the gastric pH of said patient to at least 3.5 upon the administration of one or more of said unit dosage forms; (b) a non-steroidal anti-inflammatory drug in an amount effective to reduce or eliminate pain or inflammation in said patient upon administration of one or more of said unit dosage forms; and wherein said unit dosage form provides for the coordinated release of said acid inhibitor followed by said non-steroidal anti-inflammatory drug.

While PPI such as lansoprazole and the like and acetylsalicylic acid have already been commercially available as single agents, a dry coated tablet containing both PPI and acetylsalicylic acid is not known.

DOCUMENT LIST

Patent Documents patent document 1: WO 97/25064
patent document 2: WO 2007/064274
patent document 3: WO 2005/076987
patent document 4: WO 2002/098352

SUMMARY OF THE INVENTION

Problems to be Solved by the Invention

Provision of a preparation containing both PPI and acetylsalicylic acid as active ingredients (combination agent) has extremely high clinical usefulness. However, practicalization of a preparation containing plural active ingredients is not easy as compared to preparations containing a single active ingredient. For example, the composition of the preparation needs to be controlled such that the dissolution rate of the active ingredient is optimized upon practicalization of the preparation, since the dissolution rate of the active ingredient from the preparation can influence the time-course efficacy profile after administration. In the case of a combination agent, however, the dissolution rate of each active ingredient needs to be optimized, and pharmaceutical difficulty is high. It is also necessary to suppress an adverse influence caused by interactions of plural active ingredients contained in a combination agent (decrease of preservation or chemical stability such as time-course decomposition of active ingredients, low activity and the like, decrease of dissolution stability such as time-course change of active ingredient dissolution pattern and the like, and the like).

Furthermore, the development of a dry coated tablet that can be taken easily while maintaining the handling convenience, which is the characteristics of tablet, is desired along with the aging of the population and/or change of life environment.

The present inventors have conducted intensive studies and found that a dry coated tablet containing an enteric-coated tablet containing acetylsalicylic acid as an inner core and enteric micro granules containing a proton pump inhibitor in an outer layer thereof shows high stability of the active ingredients (acetylsalicylic acid and PPI), and expresses the pharmacological effects of the active ingredients stably and rapidly after administration, which resulted in the completion of the present invention.

Means of Solving the Problems

Accordingly, the present invention provides
[1] a dry coated tablet having an inner core and an outer layer, wherein the inner core is an enteric-coated tablet containing acetylsalicylic acid, and the outer layer contains enteric micro granules containing a proton pump inhibitor,
[2] the dry coated tablet of the above-mentioned [1], which is a plain tablet,
[3] the dry coated tablet of the above-mentioned [1], wherein the proton pump inhibitor is lansoprazole, omeprazole, rabeprazole, pantoprazole or an optically active form thereof or a salt thereof,
[4] the dry coated tablet of the above-mentioned [1], wherein the content of acetylsalicylic acid is 70 mg-120 mg per one dry coated tablet,
[5] the dry coated tablet of the above-mentioned [1], wherein the inner core further contains carmellose,
[6] the dry coated tablet of the above-mentioned [1], wherein the outer layer contains at least one kind selected from crospovidone and magnesium alumino metasilicate in a part other than the enteric micro granules containing a proton pump inhibitor,
[7] the dry coated tablet of the above-mentioned [1], wherein the enteric coating in the inner core comprises a methacrylic acid copolymer LD and an ethyl acrylate-methyl methacrylate copolymer,
[8] the dry coated tablet of the above-mentioned [7], wherein the content ratio of the methacrylic acid copolymer LD and the ethyl acrylate-methyl methacrylate copolymer is 85:15-95:5,
[9] the dry coated tablet of the above-mentioned [1], wherein the acetylsalicylic acid and the proton pump inhibitor each show an acid resistance rate of not more than 10%,
[10] the dry coated tablet of the above-mentioned [1], wherein the difference in the diameter between the inner core and the dry coated tablet is not less than 2.0 mm before enteric coating of the inner core,
[11] the dry coated tablet of the above-mentioned [1], wherein the weight ratio of the inner core and the outer layer is 1:2-1:6,
[12] a method of producing a dry coated tablet, comprising mixing enteric micro granules containing a proton pump inhibitor with a diluent, granulating the mixture, and tableting the obtained granules together with an enteric-coated tablet containing acetylsalicylic acid and an optionally added additive,
[13] the production method of the above-mentioned [12], wherein the enteric-coated tablet containing acetylsalicylic acid is produced from acetylsalicylic acid wherein not less than 80 wt % has a particle size of about 125-about 1000 μm as a starting material, and
[14] a dry coated tablet obtained by the production method of the above-mentioned [12] or [13].

Effect of the Invention

The dry coated tablet of the present invention can be administered for the treatment or suppression of the onset of gastric ulcer or duodenal ulcer while continuing administration of acetylsalicylic acid, since it contains (1) PPI having a strong acid secretion suppressive action and (2) acetylsalicylic acid useful as a prophylactic and/or therapeutic agent for diseases of cerebrovascular or circulatory, for example, a thrombus and/or embolization inhibitor for angina pectoris (chronic stable angina pectoris, unstable angina pectoris), myocardial infarction; a prophylactic and/or therapeutic agent for ischemic cerebrovascular disorder (transient ischemic attack (TIA), cerebral infarction); a thrombus and/or embolization inhibitor used after coronary-artery bypass surgery (CABG) or percutaneous transluminal coronary angioplasty (PTCA); or a prophylactic and/or therapeutic agent for Kawasaki disease (including cardiovascular sequelae due to Kawasaki disease).

Moreover, since acetylsalicylic acid can also be used as one kind of non-steroidal anti-inflammatory drug for the treatment of mainly pain, fever and inflammation, the dry coated tablet of the present invention can be administered for the treatment or suppression of the onset of gastric ulcer or duodenal ulcer while continuing administration of a non-steroidal anti-inflammatory drug.

The dry coated tablet of the present invention shows high stability of the active ingredients (acetylsalicylic acid and PPI), and expresses a pharmacological effect of the active ingredients stably and rapidly after administration.

The dry coated tablet of the present invention can be easily administered while maintaining the convenience of handling.

The dry coated tablet of the present invention and a dry coated tablet produced by the production method of the present invention are superior in tablet strength, dissolution property of active ingredients (acetylsalicylic acid and PPI), preservation stability and acid resistance.

DESCRIPTION OF EMBODIMENTS

Figure 1:
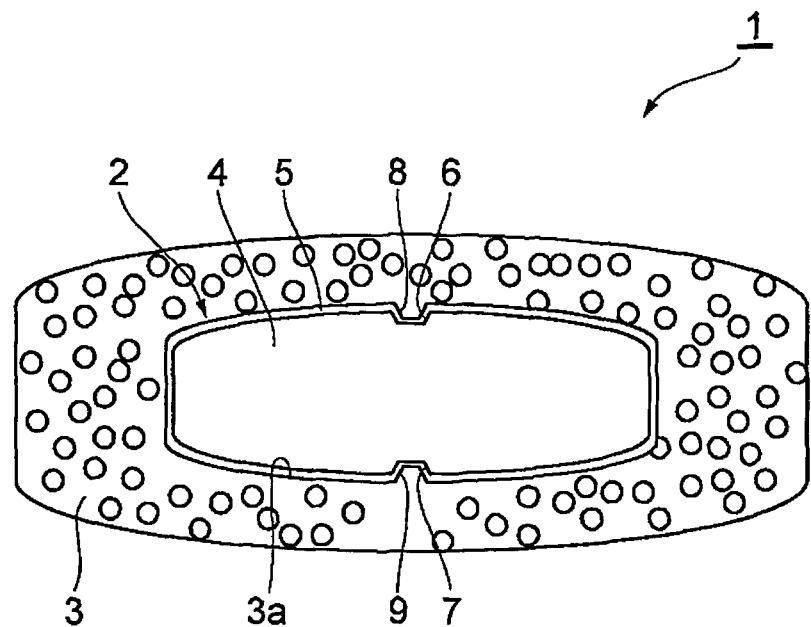
FIG. 1 is a schematic view showing one embodiment of the dry coated tablet of the present invention.
Figure 2:
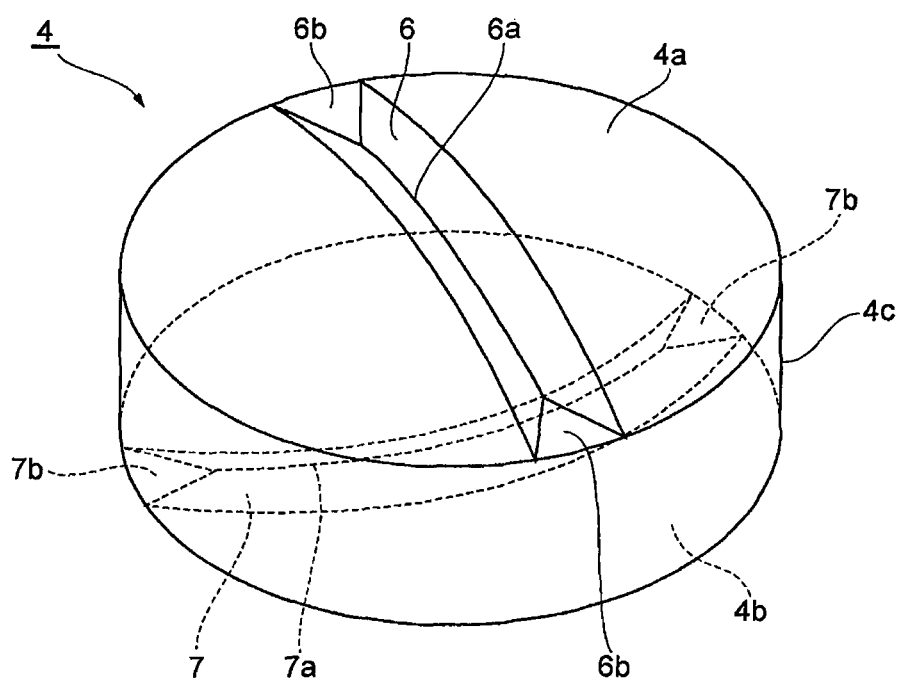
FIG. 2 is a perspective view showing one embodiment of a plain tablet in the inner core of the dry coated tablet of the present invention.
Figure 3:
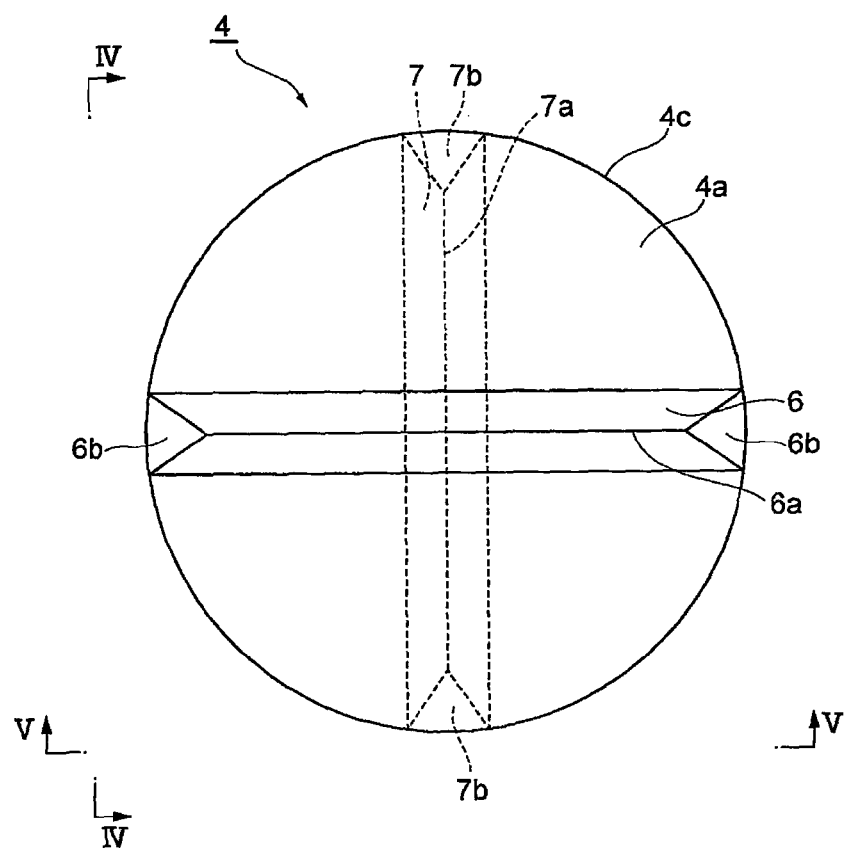
FIG. 3 is a plan view showing one embodiment of a plain tablet in the inner core of the dry coated tablet of the present invention.

The present invention is explained in detail in the following.

The dry coated tablet of the present invention is characterized in that it contains an inner core which is an "enteric-coated tablet containing acetylsalicylic acid", and "enteric micro granules containing a proton pump inhibitor" in the outer layer thereof.
(1) "enteric-coated tablet containing acetylsalicylic acid" to (hereinafter sometimes to be referred to as "inner core tablet")

The "enteric-coated tablet containing acetylsalicylic acid" in the dry coated tablet of the present invention contains 1) acetylsalicylic acid, 2) an optionally added additive and 3) an enteric coating component, and constitutes an inner core of the dry coated tablet.

The "enteric-coated tablet containing acetylsalicylic acid" can be produced by mixing 1) acetylsalicylic acid and 2) an optionally added additive, tableting the mixture to give "a plain tablet containing acetylsalicylic acid", and coating same with 3) an enteric coating component.

Here, "coating" means not only covering the entire surface of a target to be coated (plain tablet containing acetylsalicylic acid) but also partial covering, adsorption and absorption.

The content of acetylsalicylic acid in the dry coated tablet of the present invention is generally about 70-about 400 mg per one dry coated tablet. When treatment of mainly pain, fever or inflammation is desired as a non-steroidal anti-inflammatory drug, the content of acetylsalicylic acid in the dry coated tablet of the present invention is generally about 250-about 400 mg per one dry coated tablet.

On the other hand, when suppression of thrombus and/or embolization and the like is desired in cerebrovascular or circulatory diseases (antiplatelet therapy), the content of acetylsalicylic acid in the dry coated tablet of the present invention is generally about 70 mg-about 120 mg (preferably about 100 mg) per one dry coated tablet.

The content of acetylsalicylic acid in the dry coated tablet is generally about 10-about 50 wt %.

As the aforementioned "optionally added additive", diluent, disintegrant, fluidizer, binder, surfactant, lubricant and the like are used.

Examples of the aforementioned "diluent" include lactose, sucrose, D-mannitol, starch, cornstarch, microcrystalline cellulose, light anhydrous silicic acid and the like. These diluents may be used alone or two or more kinds thereof may be used in combination. The content of the "diluent" is generally about 5-about 30 wt %, preferably about 10-about 20 wt % of the "enteric-coated tablet containing acetylsalicylic acid".

Examples of the aforementioned "disintegrant" include carmellose, croscarmellose sodium, microcrystalline cellulose, pregelatinized starch, gelatin, low-substituted hydroxypropylcellulose and the like. These may be used alone or two or more kinds thereof may be used in combination. Particularly, carmellose is preferably used from the aspects of disintegration property of acetylsalicylic acid and improvement of the stability. The content of the "disintegrant" is generally about 1-about 20 wt %, preferably about 1-about 10 wt %, of the "enteric-coated tablet containing acetylsalicylic acid".

Examples of the aforementioned "fluidizer" include light anhydrous silicic acid, hydrated silicon dioxide, talc, stearic acid and the like can be mentioned. These may be used alone or two or more kinds thereof may be used in combination. The content of the "fluidizer" is generally 0-about 10 wt % of the "enteric-coated tablet containing acetylsalicylic acid".

Examples of the aforementioned "binder" include hydroxypropylcellulose, cornstarch, hydroxypropylmethylcellulose, microcrystalline cellulose, pregelatinized starch, polyvinylpyrrolidone, gum arabic powder, gelatin, pullulan, low-substituted hydroxypropylcellulose and the like. These may be used alone or two or more kinds thereof may be used in combination. The content of the "binder" is generally 0-about 10 wt % of the "enteric-coated tablet containing acetylsalicylic acid".

Examples of the aforementioned "surfactant" include sodium lauryl sulfate, polyoxyethylene-polyoxypropyleneglycol, polysorbate 80 and the like. These may be used alone or two or more kinds thereof may be used in combination.

Examples of the aforementioned "lubricant" include hydrogenated oil, sodium lauryl sulfate, stearic acid, polysorbate 80 and the like. Lubricants such as magnesium stearate and the like show poor compatibility with acetylsalicylic acid, it is preferable to not contain a lubricant such as magnesium stearate and the like in a plain tablet in the inner core of the dry coated tablet of the present invention.

As the aforementioned additive, diluent, disintegrant, binder and the like are preferably used.

As a mixture of acetylsalicylic acid and an additive, a powder of acetylsalicylic acid, or a premix of acetylsalicylic acid and a diluent (e.g., acetylsalicylic acid:cornstarch=90:10 dry-type granulation product) may be uniformly mixed with other additive. To avoid tableting trouble and poor flowability, an acetylsalicylic acid granulation product having a large particle size is desirably mixed uniformly with an additive, and the mixture is tableted to give a plain tablet containing acetylsalicylic acid. As the aforementioned acetylsalicylic acid granulation product, an acetylsalicylic acid wherein not less than 80 wt % has a particle size of about 125-about 1000 μm is preferable. The above-mentioned particle size and particle size distribution can be measured, for example, by sieving acetylsalicylic acid using sieves with aperture 125 μm and 1000 μm.

The "mixing" of acetylsalicylic acid and additive is performed by a general mixing method, for example, mixing, kneading, granulation and the like. The "mixing" is performed using an apparatus, for example, vertical granulator VG10 (manufactured by POWREX CORPORATION), universal kneader (manufactured by HATA IRON WORKS CO., LTD.), fluid-bed granulator LAB-1, FD-3S, FD-WSG-60 (manufactured by POWREX CORPORATION), V-type mixer, tumbler mixer and the like.

The "tableting" is performed by punching at a pressure of 1-80 kN/cm$^2$, 10-70 kN/cm$^2$, preferably 15-60 kN/cm$^2$, using a single punch tableting machine, a rotary tableting machine (manufactured by Kikusui Seisakusho Ltd.) and the like. When using a rotary tableting machine, tableting is performed at general rotation, for example, 3-80 min$^{-1}$, preferably 3-60 min$^{-1}$, more preferably 5-40 min$^{-1}$.

A preferable diameter of "a plain tablet containing acetylsalicylic acid" is 5.0-8.0 mm.

The shape of "a plain tablet containing acetylsalicylic acid" corresponds to a desired shape of the inner core. The shape of the inner core is mentioned below.

Examples of the "enteric coating component" used to coat "a plain tablet containing acetylsalicylic acid" include aqueous enteric polymer bases such as cellulose acetate phthalate (CAP (trade name; manufactured by Aquateric FMC)), hydroxypropylmethylcellulose phthalate (HP-55 (trade name; manufactured by Shin-Etsu Chemical Co., Ltd.)), hydroxymethylcellulose acetate succinate, methacrylic acid copolymer (e.g., methacrylic acid copolymer LD (Eudragit L30D-55 (trade name; manufactured by EVONIK INDUSTRIES)), Kollicoat MAE30DP (trade name; manufactured by BASF), Polyquid PA30 (trade name; manufactured by Sanyo Chemical Industries Ltd.) and the like), carboxymethylethylcellulose, shellac and the like; sustained-release bases such as methacrylate copolymer (e.g., ethyl acrylate methyl-methacrylate copolymer (Eudragit NE30D (trade name; manufactured by EVONIK INDUSTRIES)), Ammonioalkyl Methacrylate Copolymer Dispersion, Type A (Eudragit RL30D (trade name; manufactured by EVONIK INDUSTRIES)), aminoalkylmethacrylate copolymer RS (Eudragit RS30D (trade name; manufactured by EVONIK INDUSTRIES)) and the like) and the like; water-soluble polymers such as ethanol-soluble water-soluble polymer (e.g., cellulose derivatives such as hydroxypropylcellulose (hereinafter sometimes to be described as HPC) and the like, polyvinylpyrrolidone and the like), ethanol-insoluble water-soluble polymer (e.g., hydroxypropylmethylcellulose (hereinafter sometimes to be described as HPMC), cellulose derivatives such as methylcellulose, carmellose sodium and the like, sodium polyacrylate, polyvinyl alcohol, sodium alginate, guar gum and the like) and the like; plasticizers such as triethyl citrate, polyethylene glycol, acetylated monoglyceride, triacetin, castor oil and the like; and the like. These may be used alone or two or more kinds thereof may be used in combination.

As the aforementioned "aqueous enteric polymer base", methacrylic acid copolymers such as methacrylic acid copolymer LD and the like are preferable. The content of the "aqueous enteric polymer base" is generally about 3-about 20 wt % of the "enteric-coated tablet containing acetylsalicylic acid".

As the aforementioned "sustained-release base", methacrylate copolymers such as ethyl acrylate-methyl methacrylate copolymer and the like are preferable. The content of the "sustained-release base" is generally about 0.3-about 1.0 wt % of the "enteric-coated tablet containing acetylsalicylic acid". The content of the "sustained-release base" is generally about 5-about 30 parts by weight, preferably about 5-about 15 parts by weight, per 100 parts by weight of the aqueous enteric polymer base.

As the aforementioned "plasticizer", triethyl citrate and the like are preferable. The content of the "plasticizer" is generally about 0.5-about 3.0 wt % of the "enteric-coated tablet containing acetylsalicylic acid". The content of the "plasticizer" is preferably about 10-about 30 parts by weight per 100 parts by weight of the aqueous enteric polymer base.

As the polymer constituting the enteric coating layer of the "enteric-coated tablet containing acetylsalicylic acid", a coating agent containing an aqueous enteric polymer base and a sustained-release base is preferably used to avoid breakage of the enteric coating layer of inner core in a dry coating tableting step. Use of a coating solution containing a methacrylic acid copolymer such as methacrylic acid copolymer LD and the like, and a methacrylate copolymer such as ethyl acrylate methyl-methacrylate copolymer and the like at a given ratio is particularly desirable.

For example, a preferable content ratio of a methacrylic acid copolymer such as methacrylic acid copolymer LD and the like, and a methacrylate copolymer such as ethyl acrylate methyl-methacrylate copolymer and the like (methacrylic acid copolymer (particularly methacrylic acid copolymer LD): methacrylate copolymer (particularly ethyl acrylate-ethyl methacrylate copolymer)) is about 85:15-about 95:5, particularly preferably about 9:1.

The aforementioned "enteric coating component" may contain, in addition to the aforementioned aqueous enteric polymer base, sustained-release base, water-soluble polymer and plasticizer, various additives such as surfactant, lubricant, pH adjuster and the like.

Examples of the aforementioned "surfactant" include polysorbate (e.g., polysorbate 80), polyoxyethylene-polyoxypropylene copolymer, sodium lauryl sulfate and the like. Of these, polysorbate and sodium lauryl sulfate are preferable. The content of the "surfactant" is generally about 1-about 5 wt % of the enteric coating component.

Examples of the aforementioned "lubricant" include talc, glycerol monostearate and the like, with preference given to glycerol monostearate. The content of the "lubricant" is generally about 1-about 30 wt % of the enteric coating component.

Examples of the aforementioned "pH adjuster" include citric anhydride. The content of the "pH adjuster" is generally 0-about 2 wt % of the enteric coating component.

The aforementioned "enteric-coated tablet containing acetylsalicylic acid" can be produced by applying an "enteric coating component" to "a plain tablet containing acetylsalicylic acid" by a known coating method.

While the coating method is not particularly limited, for example, an enteric coating component is applied to a plain tablet by a coating machine such as a film coating machine and the like.

The proportion of the coating layer relative to the "plain tablet containing acetylsalicylic acid" can be selected from the range permitting control of acid resistance and dissolution property of acetylsalicylic acid. For example, it is generally about 3-about 30 parts by weight, preferably about 5-about 20 parts by weight, per 100 parts by weight of the plain tablet.

The "coating layer" may be formed by plural layers, and combination of various coating layers such as a base coating layer, enteric coating layer and the like is appropriately selected as necessary.

A coating solution for enteric coating is, for example, a mixture of enteric coating components such as the aforementioned aqueous enteric polymer base, sustained-release base, water-soluble polymer, plasticizer, surfactant, lubricant, pH adjuster and the like. The mixture may be a solution or a dispersion, and can be prepared using water or organic solvent such as ethanol and the like, or a mixed solution thereof. The concentration of polymers such as aqueous enteric polymer base, sustained-release base, water-soluble polymer and the like in the mixture is generally about 0.1-about 50 wt %, preferably about 5-about 30 wt %.

Where necessary, an lubricant or a binder, or both may be applied on the outer side of the enteric coating layer, which increases the tablet strength. Examples of the binder to be applied on the outer side of the enteric coating layer include hydroxypropylcellulose, hydroxypropylmethylcellulose, pregelatinized starch, polyvinylpyrrolidone, gum arabic powder, gelatin, pullulan and the like. Examples of the diluent to be applied on the outer side of the enteric coating layer include lactose, sucrose, mannitol, xylitol, erythritol, starch, cornstarch, microcrystalline cellulose, light anhydrous silicic acid and the like. A diluent can be prepared into a solution or suspension together with a binder and used for coating.

A preferable shape of the inner core (that is, inner core tablet) of the dry coated tablet of the present invention is explained in the following.

The outer surface of the inner core preferably has a concave part with an opening larger than the smallest average particle size of the solid powder components contained in the outer layer.

Due to the opening larger than the smallest average particle size of the solid powder components contained in the outer layer, at least one kind of powder solid component enters the concave part when forming the outer layer on the outer surface of the inner core and the strength of the dry coated tablet can be increased.

The depth of the concave part is preferably larger than the smallest average particle size of the solid powder components contained in the outer layer. In this case, the strength of the dry coated tablet can be further increased.

The concave part may be formed in a groove, or perforation dispersed on the outer surface of the inner core. The concave part may be a letter, number, symbol etc. formed like a groove.

When the inner core has two surfaces disposed to face each other, the concave part may be formed on at least one of the two surfaces. In this case, the outer layer is compressed along the opposing direction of the two surfaces, and the inner surface of the outer layer can more certainly enter into the concave part formed on at least one of the two surfaces.

When the inner core has two surfaces disposed to face each other and a peripheral surface disposed between the two edges of the two surfaces, the concave part may be formed on the peripheral surface.

FIG. 1 is a schematic view showing one embodiment of the dry coated tablet of the present invention.

As shown in FIG. 1, the outer layer 3 is formed to enclose the inner core 2, and has a shape corresponding to the shape of the inner core 2. Grooves 8, 9 are filled with the components contained in the outer layer 3. That is, the inner surface 3a of the outer layer 3 enters into grooves 8, 9. Grooves corresponding to grooves 8, 9 are not formed on the surface of the outer layer 3, and the surface of the outer layer 3 is smooth.

The shape of the inner core is explained in more detail. FIGS. 2-8 show one embodiment of the inner core or its plain tablet in the dry coated tablet of the present invention.

As shown in FIGS. 2-5, the plain tablet 4 in the inner core 2 has a flat round shape in a plan view. To be specific, plain tablet 4 has round surfaces 4a, 4b facing each other, and a peripheral surface 4c formed between the edges of the round surfaces 4a, 4b, wherein the distance between the end portions of the plain tablet 4 in the opposing direction of the round surfaces 4a, 4b is smaller than the diameter of the plain tablet 4 in a plan view. Each of the round surfaces 4a, 4b swells spherically. Thus, the plain tablet 4 has a tablet shape with, what is called, a round shape (R). The diameter of the plain tablet 4 in a plan view is, for example, about 5 mm-about 8 mm. The radius of the curvature formed by the round surfaces 4a, 4b is larger than the radius of the plain tablet 4 in a plan view and, for example, about 10 mm.

The round surfaces 4a, 4b have grooves (concave parts) 6, 7 formed along the diameter direction of the round surfaces 4a, 4b. The grooves 6, 7 are orthogonal to each other in a plan view. While the grooves 6, 7 do not always need to be orthogonal to each other in a plan view, it is preferable that they are. Each cross sectional shape of the grooves 6, 7 is V-shaped, and the width of the grooves 6, 7 increases as it gets farther from the bottom part. The bottom parts 6a, 7a of the grooves 6, 7 curve following the sphere formed by the round surfaces 4a, 4b. The both end portions of the groove 6 have end surfaces 6b, 6b, which correspond to the flat plane including the periphery of the round surface 4a, and the both end portions of the groove 7 have end surfaces 7b, 7b, which correspond to the flat plane including the periphery of the round surface 4b. The grooves 6, 7 are formed with a tableting punch (mold) during tableting of the plain tablet 4. When concave parts such as the grooves 6, 7 and the like are formed, the surrounding parts relatively become convex parts. That is, forming a concave part is the same as forming a convex part.

Figure 4:
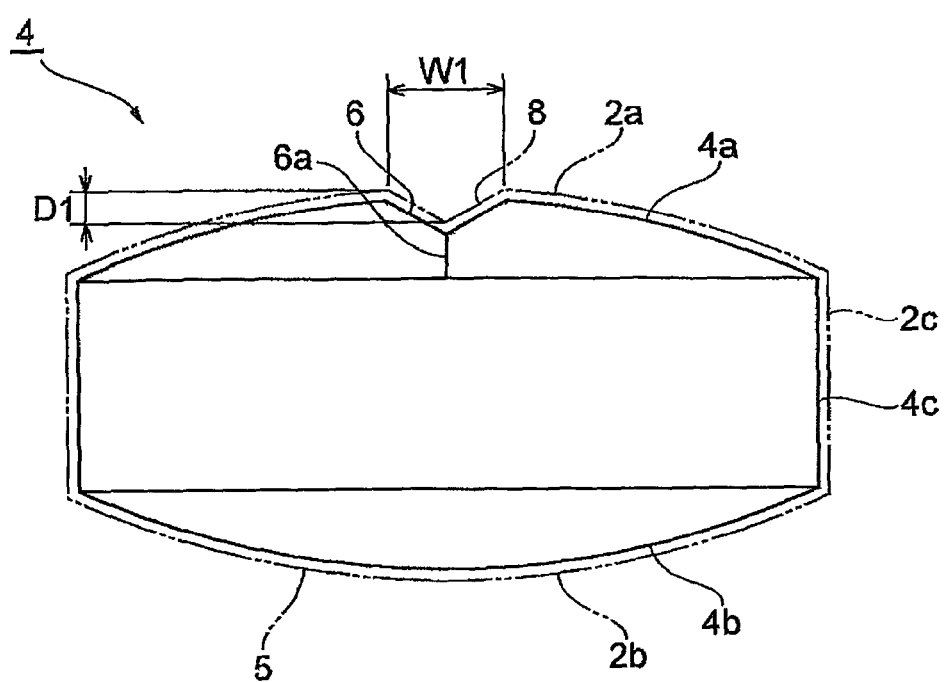
FIG. 4 is an arrow view along line IV-IV in FIG. 3.
Figure 5:
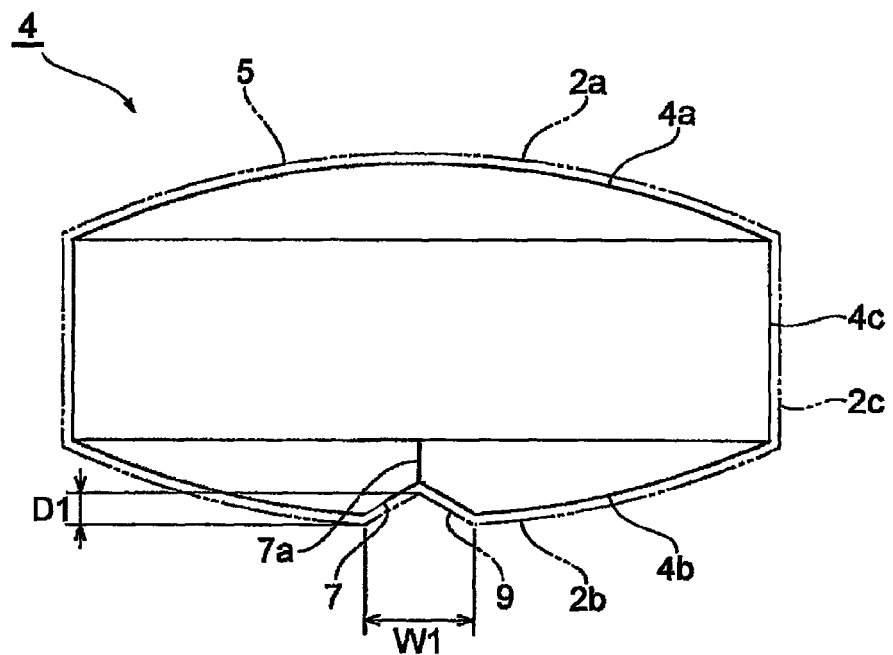
FIG. 5 is an arrow view along line V-V in FIG. 3.

The inner core 2 is formed by coating the outer surface of the plain tablet 4 with a coating layer 5. After formation of the coating layer 5, the inner core 2 has a flat round shape in a plan view like the plain tablet 4. As shown in FIG. 4 and FIG. 5, coating layer 5 is formed on the round surfaces 4a, 4b of the plain tablet 4 to form round surfaces 2a, 2b of the inner core 2. A coating layer 5 is formed on the peripheral surface 4c of the plain tablet 4 to form a peripheral surface 2c of the inner core 2. The coating layer 5 enters into the grooves 6, 7 of the plain tablet 4 to form grooves 8, 9 having a V-shaped section in the round surfaces 2a, 2b of the inner core 2. The opening width W1 of the grooves 8, 9 of the inner core 2 is larger than at least the smallest average particle size of a solid powder component contained in the outer layer 3. The opening width W1 is preferably larger than the largest average particle size of a solid powder component contained in the outer layer 3.

The depth D1 of the grooves 8, 9 of the inner core 2 is also preferably larger than at least the smallest average particle size of a solid powder component contained in the outer layer 3, and preferably larger than the largest average particle size of a solid powder component contained in the outer layer 3.

The "average particle size" of each solid powder component contained in the outer layer 3 means a volume standard median size (median size: particle size corresponding to 50% of accumulation distribution). As the measurement method thereof, a laser diffraction particle size distribution measurement method can be mentioned, which is specifically a method using laser diffraction particle size analyzer HEROS RODOS (manufactured by Sympatec (Germany)).

Figure 6:
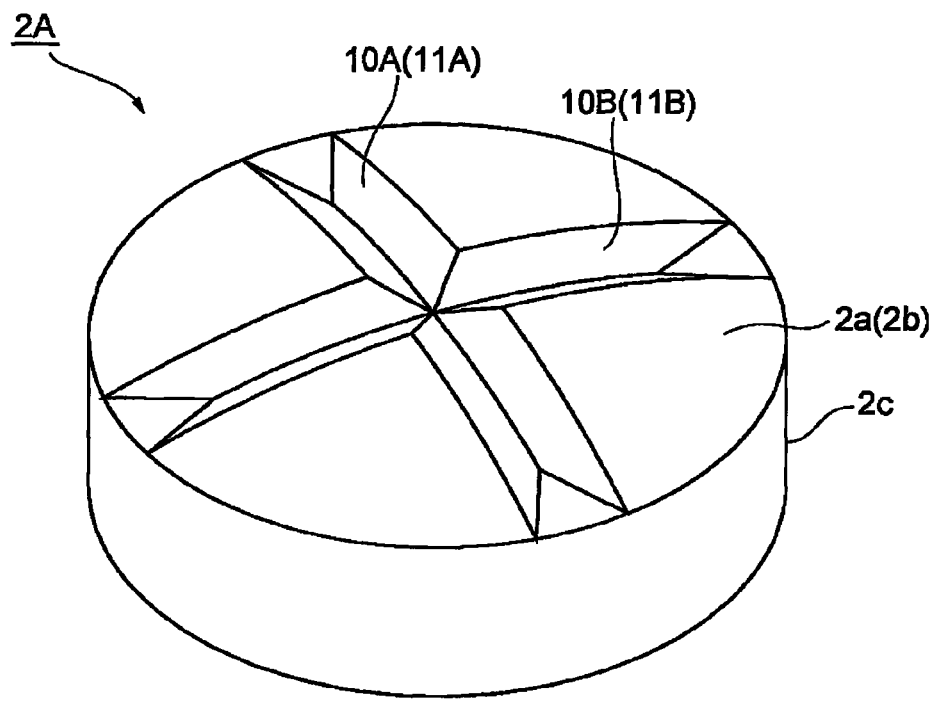
FIG. 6 is a perspective view showing one embodiment of a plain tablet in the inner core of the dry coated tablet of the present invention.

The inner core 2A shown in FIG. 6 has grooves 10A, 10B along cross-like lines that intersect at the center of an inside surface 2a, and also similar grooves 11A, 11B on an inside surface 2b. The grooves 10A, 10B and the grooves 11A, 11B may be inclined with each other in a plan view.

Figure 7:
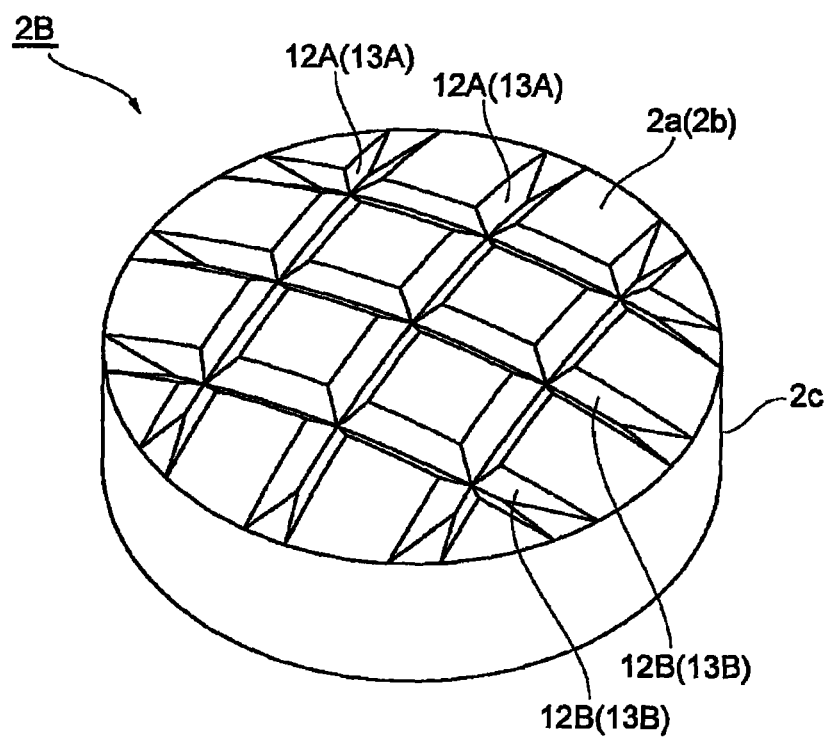
FIG. 7 is a perspective view showing one embodiment of a plain tablet in the inner core of the dry coated tablet of the present invention.

In inner core 2B shown in FIG. 7, plural grooves 12A, 12A along the lines parallel to each other and plural grooves 12B, 12B along the lines perpendicular to each groove 12A are formed in a lattice mesh on round surface 2a, and also similar grooves 13A, 13A and grooves 13B, 13B in a lattice mesh on round surface 2b.

Figure 8:
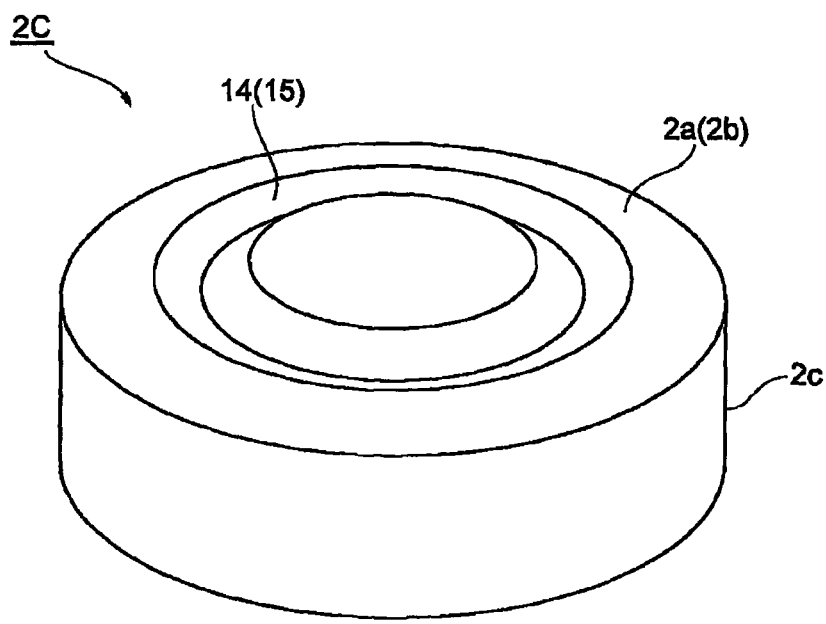
FIG. 8 is a perspective view showing one embodiment of a plain tablet in the inner core of the dry coated tablet of the present invention.

In the inner core 2C shown in FIG. 8, grooves 14, 15 are formed on each of round surfaces 2a, 2b along a round shape corresponding to the end portion. In this case, each diameter direction of the inner core 2C and the grooves 14, 15 intersect at an equal angle. Therefore, an action to prevent misalignment between the inner core 2 and the outer layer 3 is obtained more uniformly in each diameter direction of the inner core 2.

(2) "Enteric Micro Granules Containing PPI"

(2)-1: PPI

In the present invention, a compound represented by the following formula (I) [hereinafter to be sometimes simply referred to as compound (I)] or an optically active form thereof or a salt thereof is preferable as PPI.

Formula (I)

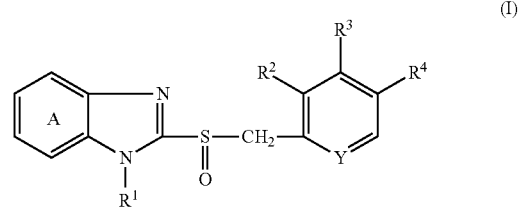

wherein ring A is a benzene ring optionally having substituent(s), $R^1$ is a hydrogen atom, an aralkyl group optionally having substituent(s), an acyl group or an acyloxy group, $R^2$, $R^3$ and $R^4$ are the same or different and each is a hydrogen atom, an alkyl group optionally having substituent(s), an alkoxy group optionally having substituent(s) or an amino group optionally having substituent(s), and Y is a nitrogen atom or CH, or an optically active form thereof or a salt thereof.

In the above-mentioned compound (I), examples of the "substituent" of the "benzene ring optionally having substituent(s)" for ring A include a halogen atom, a cyano group, a nitro group, an alkyl group optionally having substituent(s), a hydroxy group, an alkoxy group optionally having substituent(s), an aryl group, an aryloxy group, a carboxy group, an acyl group, an acyloxy group, a 5- to 10-membered heterocyclic group and the like. The benzene ring may be substituted by about 1 to 3 of these substituents. When the number of substituents is two or more, each substituent may be the same or different. Of these substituents, a halogen atom, an alkyl group optionally having substituent(s), an alkoxy group optionally having substituent(s) and the like are preferable.

Examples of the halogen atom include fluorine, chlorine, bromine atom and the like. Of these, a fluorine atom is preferable.

Examples of the "alkyl group" of the "alkyl group optionally having substituent(s)" include a $C_{1-7}$ alkyl group (e.g., methyl, ethyl, propyl, isopropyl, butyl, isobutyl, sec-butyl, tert-butyl, pentyl, hexyl, heptyl group etc.) and the like. Examples of the "substituent" of the "alkyl group optionally having substituent(s)" include a halogen atom, a hydroxy group, a $C_{1-6}$ alkoxy group (e.g., methoxy, ethoxy, propoxy, butoxy etc.), a $C_{1-6}$ alkoxy-carbonyl group (e.g., methoxycarbonyl, ethoxycarbonyl, propoxycarbonyl etc.), a carbamoyl group and the like, and the number of these substituents may be about 1 to 3. When the number of substituents is two or more, each substituent may be the same or different.

Examples of the "alkoxy group" of the "alkoxy group optionally having substituent(s)" include a $C_{1-6}$ alkoxy group (e.g., methoxy, ethoxy, propoxy, isopropoxy, butoxy, isobutoxy, pentoxy etc.) and the like. Examples of the "substituent" of the "alkoxy group optionally having substituent(s)" include those similar to the "substituent" of the above-mentioned "alkyl group optionally having substituent(s)", and the number of substituents is the same.

Examples of the "aryl group" include a $C_{6-14}$ aryl group (e.g., phenyl, 1-naphthyl, 2-naphthyl, biphenyl, 2-anthryl etc.) and the like.

Examples of the "aryloxy group" include a $C_{6-14}$ aryloxy group (e.g., phenyloxy, 1-naphthyloxy, 2-naphthyloxy etc.) and the like.

Examples of the "acyl group" include formyl, alkylcarbonyl, alkoxycarbonyl, carbamoyl, alkylcarbamoyl, alkylsulfinyl, alkylsulfonyl and the like.

Examples of the "alkylcarbonyl group" include a $C_{1-6}$ alkyl-carbonyl group (e.g., acetyl, propionyl etc.) and the like.

Examples of the "alkoxycarbonyl group" include a $C_{1-6}$ alkoxy-carbonyl group (e.g., methoxycarbonyl, ethoxycarbonyl, propoxycarbonyl, butoxycarbonyl etc.) and the like.

Examples of the "alkylcarbamoyl group" include an N—$C_{1-6}$ alkyl-carbamoyl group (e.g., methylcarbamoyl, ethylcarbamoyl group etc.), an N,N-di-$C_{1-6}$ alkyl-carbamoyl group (e.g., N,N-dimethylcarbamoyl, N,N-diethylcarbamoyl etc.) and the like.

Examples of the "alkylsulfinyl group" include a $C_{1-7}$ alkylsulfinyl group (e.g., methylsulfinyl, ethylsulfinyl, propylsulfinyl, isopropylsulfinyl etc.) and the like.

Examples of the "alkylsulfonyl group" include a $C_{1-7}$ alkylsulfonyl group (e.g., methylsulfonyl, ethylsulfonyl, propylsulfonyl, isopropylsulfonyl etc.) and the like.

Examples of the "acyloxy group" include alkylcarbonyloxy, alkoxycarbonyloxy, carbamoyloxy, alkylcarbamoyloxy, alkylsulfinyloxy, alkylsulfonyloxy and the like.

Examples of the "alkylcarbonyloxy group" include a $C_{1-6}$ alkyl-carbonyloxy group (e.g., acetyloxy, propionyloxy etc.) and the like.

Examples of the "alkoxycarbonyloxy group" include a $C_{1-6}$ alkoxy-carbonyloxy group (e.g., methoxycarbonyloxy, ethoxycarbonyloxy, propoxycarbonyloxy, butoxycarbonyloxy etc.) and the like.

Examples of the "alkylcarbamoyloxy group" include a $C_{1-6}$ alkyl-carbamoyloxy group (e.g., methylcarbamoyloxy, ethylcarbamoyloxy etc.) and the like.

Examples of the "alkylsulfinyloxy group" include a $C_{1-7}$ alkylsulfinyloxy group (e.g., methylsulfinyloxy, ethylsulfinyloxy, propylsulfinyloxy, isopropylsulfinyloxy etc.) and the like.

Examples of the "alkylsulfonyloxy group" include a $C_{1-7}$ alkylsulfonyloxy group (e.g., methylsulfonyloxy, ethylsulfonyloxy, propylsulfonyloxy, isopropylsulfonyloxy etc.) and the like.

Examples of the "5- to 10-membered heterocyclic group" include a 5- to 10-membered (preferably 5- or 6-membered) heterocyclic group containing, besides carbon atom, one or more (e.g., 1-3) hetero atoms selected from nitrogen atom, sulfur atom and oxygen atom and the like. Specific examples include 2- or 3-thienyl group, 2-, 3- or 4-pyridyl group, 2- or 3-furyl group, 1-, 2- or 3-pyrrolyl group, 2-, 3-, 4-, 5- or 8-quinolyl group, 1-, 3-, 4- or 5-isoquinolyl group, 1-, 2- or 3-indolyl group and the like. Of these, preferred is a 5- or 6-membered heterocyclic group such as 1-, 2- or 3-pyrrolyl group and the like.

Preferably, ring A is a benzene ring optionally having 1 or 2 substituents selected from a halogen atom, an optionally halogenated $C_{1-4}$ alkyl group, an optionally halogenated $C_{1-4}$ alkoxy group and a 5- or 6-membered heterocyclic group.

Examples of the "aralkyl group" of the "aralkyl group optionally having substituent(s)" for $R^1$ include a $C_{7-16}$ aralkyl group (e.g., $C_{6-10}$ aryl $C_{1-6}$ alkyl group such as benzyl, phenethyl etc., and the like) and the like. Examples of the "substituent" of the "aralkyl group optionally having substituent(s)" include substituents similar to the "substituent" of the above-mentioned "alkyl group optionally having substituent(s)", and the number of substituents is about 1 to 4. When the number of substituents is two or more, each substituent may be the same or different.

Examples of the "acyl group" for $R^1$ include the "acyl group" described as a substituent for the above-mentioned ring A and the like.

Examples of the "acyloxy group" for $R^1$ include the "acyloxy group" described as a substituent for the above-mentioned ring A and the like.

Preferable $R^1$ is a hydrogen atom.

Examples of the "alkyl group optionally having substituent(s)" for $R^2$, $R^3$ or $R^4$ include the "alkyl group optionally having substituent(s)" described as a substituent for the above-mentioned ring A and the like.

Examples of the "alkoxy group optionally having substituent(s)" for $R^2$, $R^3$ or $R^4$ include the "alkoxy group optionally having substituent(s)" described as the substituent for the above-mentioned ring A and the like.

Examples of the "amino group optionally having substituent(s)" for $R^2$, $R^3$ or $R^4$ include an amino group, a mono-$C_{1-6}$ alkylamino group (e.g., methylamino, ethylamino etc.), a mono-$C_{6-14}$ arylamino group (e.g., phenylamino, 1-naphthylamino, 2-naphthylamino etc.), a di-$C_{1-6}$ alkylamino group (e.g., dimethylamino, diethylamino etc.), a di-$C_{6-14}$ arylamino group (e.g., diphenylamino etc.) and the like.

Preferable $R^2$ is a $C_{1-6}$ alkyl group, a $C_{1-6}$ alkoxy group, a $C_{1-6}$ alkoxy-$C_{1-6}$ alkoxy group or a di-$C_{1-6}$ alkylamino group. More preferable $R^2$ is a $C_{1-3}$ alkyl group or a $C_{1-3}$ alkoxy group.

Preferable $R^3$ is a hydrogen atom, a $C_{1-6}$ alkoxy-$C_{1-6}$ alkoxy group or an optionally halogenated $C_{1-6}$ alkoxy group. More preferable $R^3$ is a $C_{1-3}$ alkoxy group which is optionally halogenated or substituted by a $C_{1-3}$ alkoxy group.

Preferable $R^4$ is a hydrogen atom or $C_{1-6}$ alkyl group. More preferable $R^4$ is a hydrogen atom or a $C_{1-3}$ alkyl group (particularly a hydrogen atom).

Preferable Y is a nitrogen atom.

Preferable compound of the formula (I) is a compound wherein ring A is a benzene ring optionally having substituent(s) selected from a halogen atom, an optionally halogenated $C_{1-4}$ alkyl group, an optionally halogenated $C_{1-4}$ alkoxy group and a 5- or 6-membered heterocyclic group, $R^1$ is a hydrogen atom, $R^2$ is a $C_{1-6}$ alkyl group, a $C_{1-6}$ alkoxy group, a $C_{1-6}$ alkoxy-$C_{1-6}$ alkoxy group or a di-$C_{1-6}$ alkylamino group, $R^3$ is a hydrogen atom, a $C_{1-6}$ alkoxy-$C_{1-6}$ alkoxy group or an optionally halogenated $C_{1-6}$ alkoxy group, $R^4$ is a hydrogen atom or a $C_{1-6}$ alkyl group, and Y is a nitrogen atom.

Of compound (I), a compound represented by the formula (Ia):

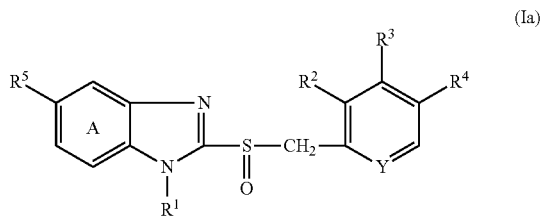

wherein $R^1$ is a hydrogen atom, $R^2$ is a $C_{1-3}$ alkyl group or a $C_{1-3}$ alkoxy group, $R^3$ is a $C_{1-3}$ alkoxy group optionally halogenated or substituted by a $C_{1-3}$ alkoxy group, $R^4$ is a hydrogen atom or a $C_{1-3}$ alkyl group, and $R^5$ is a hydrogen atom, an optionally halogenated $C_{1-3}$ alkoxy group or a pyrrolyl group (e.g., 1-, 2- or 3-pyrrolyl group).

In the formula (Ia), a compound wherein $R^1$ is a hydrogen atom, $R^2$ is a $C_{1-3}$ alkyl group, $R^3$ is an optionally halogenated $C_{1-3}$ alkoxy group, $R^4$ is a hydrogen atom, and $R^5$ is a hydrogen atom or an optionally halogenated $C_{1-3}$ alkoxy group is particularly preferable.

Specific examples of compound (I) include the following compounds.

2-[[[3-Methyl-4-(2,2,2-trifluoroethoxy)-2-pyridinyl]methyl]sulfinyl]-1H-benzimidazole, 2-[[(3,5-dimethyl-4-methoxy-2-pyridinyl)methyl]sulfinyl]-5-methoxy-1H-benzimidazole, 2-[[[4-(3-methoxypropoxy)-3-methyl-2-pyridinyl]methyl]sulfinyl]-1H-benzimidazole sodium salt, 5-difluoromethoxy-2-[[(3,4-dimethoxy-2-pyridinyl)methyl]sulfinyl]-1H-benzimidazole and the like.

Of these compounds, 2-[[[3-methyl-4-(2,2,2-trifluoroethoxy)-2-pyridinyl]methyl]sulfinyl]-1H-benzimidazole (lansoprazole) is preferable.

Compound (I) may be a racemate or an optically active form such as R-form, S-form and the like. For example, compound (I) may be an optically active form such as (R)-2-[[[3-methyl-4-(2,2,2-trifluoroethoxy)-2-pyridinyl]methyl]sulfinyl]-1H-benzimidazole and the like. In addition, the optically active form is preferable.

As a salt of compound (I) or an optically active form thereof, a pharmaceutically acceptable salt is preferable. For example, salts of compound (I) or an optically active form thereof with an inorganic base, an organic base and a basic amino acid, and the like can be mentioned.

Preferable examples of the salt with inorganic base include alkali metal salts such as sodium salt, potassium salt and the like; alkaline earth metal salts such as calcium salt, magnesium salt and the like; ammonium salt and the like.

Preferable examples of the salt with organic base include salts with alkylamine (trimethylamine, triethylamine etc.), heterocyclic amine (pyridine, picoline etc.), alkanolamine (ethanolamine, diethanolamine, triethanolamine etc.), dicyclohexylamine, N,N'-dibenzylethylene diamine and the like.

Preferable examples of the salt with basic amino acid include salts with arginine, lysine, ornithine and the like.

Of these, preferred is an alkali metal salt or an alkaline earth metal salt. Particularly, a sodium salt is preferable.

Compound (I) can be produced by a method known per se, for example, the method described in JP-A-61-50978, U.S. Pat. No. 4,628,098, JP-A-10-195068, WO98/21201 and the like or a method analogous thereto.

The optically active form of compound (I) can be obtained by a method such as an optical resolution method (fractional recrystallization, chiral column method, diastereomer method, a method using microorganism or enzyme etc.), asymmetric oxidation and the like. For example, a lansoprazole R form can be produced according to the methods described in WO00/78745, WO01/83473, WO01/87874 and WO02/44167.

The PPI to be used in the present invention is preferably selected from benzimidazole compounds having an antiulcer activity such as lansoprazole, omeprazole, rabeprazole, and pantoprazole, and optically active forms thereof and pharmaceutically acceptable salts thereof.

(2)-2: "Enteric Micro Granules Containing PPI"

In the present invention, the "enteric micro granules containing PPI" means micro granules wherein a "composition containing PPI" is coated with an enteric coating layer.

The "coating" means also partial coating and adhesion or adsorption in addition to coating the whole surface of an object (e.g., core) which is to be coated. "Average particle size" means volume based distribution median size (median size: 50% particle size from cumulative distribution), unless otherwise specified. It can be measured by, for example, a laser diffraction particle distribution measurement method. Concretely exemplified is a method using Laser Diffraction Analyzer, type: HEROS RODOS [trade name; manufactured by Sympatec (Germany)].

An average particle size of the "enteric micro granules containing PPI" is generally not more than 400 µm, preferably 300-400 µm.

Aside from the average particle size of the above "micro granules", regarding the maximum particle size, the particle size is generally practically 425 µm or less, and preferably practically 400 µm or less. Preferably, the particle size is practically preferably 300 to 425 µm, more practically preferably 300 to 400 µm.

"Practically" as used in "the particle size is practically 425 μm or less" and "the particle size is practically 400 μm or less" and the like means that the particles may include a small quantity (about 5 wt % or less) of particles whose particle size is out of above described range, to include the inevitably contaminant particles.

The content of PPI in the aforementioned "composition containing PPI" (composition before coating with enteric coating layer) is, for example, preferably not less than about 5 wt %, more preferably about 10-about 50 wt %, still more preferably about 15-about 50 wt %, particularly preferably about 20-about 50 wt %.

The content of PPI in the dry coated tablet is, for example, preferably not less than about 1 wt %, more preferably not less than about 1.5 wt %, not more than about 10.0 wt %, more preferably not less than about 2.0 wt %, not more than about 8.0 wt %.

The "composition containing PPI" preferably contains a basic inorganic salt to stabilize PPI in the preparation.

The "basic inorganic salt" includes, for example, a basic inorganic salt of sodium, potassium, magnesium and/or calcium, preferably a basic inorganic salt of magnesium and/or calcium. Among others, preferred is a basic inorganic salt of magnesium.

The basic inorganic salt of sodium includes, for example, sodium carbonate, sodium hydrogen carbonate, etc.

The basic inorganic salt of potassium includes, for example, potassium carbonate, potassium hydrogen carbonate, etc.

The basic inorganic salt of magnesium includes, for example, heavy magnesium carbonate, magnesium carbonate, magnesium oxide, magnesium hydroxide, magnesium aluminometasilicate, magnesium silicate, magnesium aluminate, synthetic hydrotalcite [$Mg_6Al_2(OH)_{16} CO_3 4H_2O$], aluminum magnesium hydroxide [$2.5 MgO Al_2O_3 xH_2O$], etc. Among others, preferred is heavy magnesium carbonate, magnesium carbonate, magnesium oxide, magnesium hydroxide, etc.

The basic inorganic salt of calcium includes, for example, precipitated calcium carbonate, calcium hydroxide, etc.

The preferable examples of the "basic inorganic salt" include heavy magnesium carbonate, magnesium carbonate, magnesium oxide, magnesium hydroxide, etc.

Such basic inorganic salt of magnesium or calcium, etc. only needs to have a basic pH (not less than 7) when it is in the form of a 1% aqueous solution or suspension.

Two or more of these basic inorganic salts (preferably a basic inorganic salt of magnesium, a basic inorganic salt of calcium, etc.) can be used as a mixture. The amount of the basic inorganic salt to be used is appropriately selected depending on the kind of the basic inorganic salt and is, for instance, about 0.3 to about 200 parts by weight, preferably about 1 to about 100 parts by weight, more preferably about 10 to about 50 parts by weight, especially preferably about 20 to about 40 parts by weight, per 100 parts by weight of PPI.

The "composition containing PPI" may contain a water-soluble polymer, and an additive generally used for the production of preparations, such as binder (e.g., hydroxypropylcellulose), disintegrant (e.g., low substituted hydroxypropylcellulose), lubricant (e.g., talc), diluent (e.g., mannitol), colorant (e.g., titanium oxide) and the like. Examples of the additive include those exemplified as the components of the below-mentioned "outer layer". The amount to be added is an amount generally used for the production of preparations. The content of the "binder" is generally about 1-about 20 wt % of the "composition containing PPI". The content of the "lubricant" is generally about 1-about 10 wt % of the "composition containing PPI". The content of the "diluent" is generally 0-about 10 wt % of the "composition containing PPI". The content of the "colorant" is generally 0-about 5 wt % of the "composition containing PPI".

The aforementioned "water-soluble polymer" includes, for example, an ethanol-soluble water-soluble polymer such as a cellulose derivative (e.g., hydroxypropyl cellulose (HPC)), poly(vinylpyrrolidone), etc.; an ethanol-insoluble water-soluble polymer such as a cellulose derivative (e.g., hydroxypropylmethyl cellulose (HPMC), methyl cellulose, carmelose sodium, etc.), sodium polyacrylate, polyvinyl alcohol, sodium alginate, and guar gum, etc.

When such water-soluble polymers are used, the dissolution of PPI can be controlled by employing them in combination with the ethanol-soluble water-soluble polymer and ethanol-insoluble water-soluble polymer or by employing them in combination with some water-soluble polymers having different viscosity.

In the present invention, the "water-soluble polymer" is preferably, a cellulose derivative such as HPC, HPMC, and methyl cellulose, and polyvinyl alcohol. More preferred is a cellulose derivative such as HPC, HPMC.

HPC contains, for example, about 53.4 to 77.5 wt %, more preferably about 60 to 70 wt %, of hydroxypropoxyl group. The viscosity of 2 wt % aqueous solution of HPC at 20° C. is generally about 1 to about 150,000 cps (centipoise). As such HPC, the Japanese Pharmacopoeia hydroxypropylcellulose and the like are used (hereinafter the viscosity of HPC is always the value of 2 wt % aqueous solution at 20° C.).

HPMC is mixed ether wherein a methoxy group and a hydroxypropoxy group are bonded. The content of the methoxy group of HPMC is, for example, about 19-about 30 wt %, and the content of the hydroxypropoxy group is, for example, about 4-about 12 wt %. The viscosity of 2 wt % aqueous solution of HPMC at 20° C. is generally about 1-about 40000 centi stokes. As such HPMC, The Japanese Pharmacopoeia hydroxypropylmethylcellulose 2208, The Japanese Pharmacopoeia hydroxypropylmethylcellulose 2906 and The Japanese Pharmacopoeia hydroxypropylmethylcellulose 2910 and the like are used. One or more kinds of hydroxypropylmethylcellulose can be used by mixing.

The content of a water-soluble polymer such as HPC and/or HPMC and the like is generally about 0.1-about 50 wt %, preferably about 1-about 30 wt %, of the "composition containing PPI" (composition before coating with enteric coating layer), since dissolution property of PPI in the composition containing PPI can be controlled and a high content of PPI can be maintained.

Examples of the "enteric coating layer" for coating the "composition containing PPI" include aqueous enteric polymer bases such as cellulose acetate phthalate (CAP (trade name; manufactured by Aquateric FMC)), hydroxypropylmethylcellulose phthalate (HP-55 (trade name; manufactured by Shin-Etsu Chemical Co., Ltd.)), hydroxymethylcellulose acetate succinate, methacrylic acid copolymer (e.g., methacrylic acid copolymer LD (Eudragit L30D-55 (trade name; manufactured by EVONIK INDUSTRIES)), Kollicoat MAE30DP (trade name; manufactured by BASF), Polyquid PA30 (trade name; manufactured by Sanyo Chemical Industries Ltd.) and the like), carboxymethylethylcellulose, shellac and the like; sustained-release bases such as methacrylate copolymer (e.g., ethyl acrylate-methyl methacrylate copolymer (Eudragit NE30D (trade name; manufactured by EVONIK INDUSTRIES)), Ammonioalkyl Methacrylate Copolymer Dispersion, Type A (Eudragit RL30D (trade name; manufactured by EVONIK INDUS- TRIES)), aminoalkylmethacrylate copolymer RS (Eudragit RS30D (trade name; manufactured by EVONIK INDUSTRIES)) and the like) and the like; water-soluble polymers such as cellulose derivatives such as ethanol-soluble water-soluble polymer (e.g., hydroxypropylcellulose (HPC) and the like, polyvinylpyrrolidone and the like), ethanol-insoluble water-soluble polymer (e.g., hydroxypropylmethylcellulose (HPMC), cellulose derivatives such as methylcellulose, carmellose sodium and the like, sodium polyacrylate, polyvinyl alcohol, sodium alginate, guar gum and the like) and the like; plasticizers such as triethyl citrate, polyethylene glycol (e.g., polyethylene glycol 6000), acetylated monoglyceride, triacetin, castor oil and the like, corrigents such as citric anhydride and the like, lubricants such as glycerol monostearate, polysorbate 80 and the like, colorants such as yellow ferric oxide, red ferric oxide, titanium oxide and the like, and the like. These may be used alone or two or more kinds thereof may be used in combination.

As the aforementioned "aqueous enteric polymer base", a methacrylic acid copolymer such as methacrylic acid copolymer LD and the like is preferable. The content of the "aqueous enteric polymer base" is generally about 40-about 90 wt % of the "enteric coating layer".

As the aforementioned "sustained-release base", methacrylate copolymers such as ethyl acrylate.methyl methacrylate copolymer and the like are preferable. The content of the "sustained-release base" is generally about 1-20 wt % of the "enteric coating layer". The content of the "sustained-release base" is generally about 5-about 30 parts by weight, preferably about 5-about 15 parts by weight, per 100 parts by weight of the aqueous enteric polymer base.

The content of the aforementioned "plasticizer" is generally about 2-about 30 wt % of the "enteric coating layer". The content of the "plasticizer" is preferably about 5-about 30 parts by weight per 100 parts by weight of the aqueous enteric polymer base.

The content of the aforementioned "corrigent" is generally 0-about 5 wt % of the "enteric coating layer".

The content of the aforementioned "lubricant" is generally about 1-about 10 wt % of the "enteric coating layer".

The content of the aforementioned "colorant" is generally 0-about 5 wt % of the "enteric coating layer".

The "enteric coating layer" preferably contains an aqueous enteric polymer base and a sustained-release base and, for example, a preferable content ratio of methacrylic acid copolymer such as methacrylic acid copolymer LD and the like, and methacrylate copolymer such as ethyl acrylate-methyl methacrylate copolymer and the like (methacrylic acid copolymer (particularly, methacrylic acid copolymer LD): methacrylate copolymer (particularly, ethyl acrylate-methyl methacrylate copolymer)) is 85:15-95:5, particularly preferably 9:1.

The "composition containing PPI" can be produced by a known granulation method.

The "granulation method" includes, for example, tumbling granulation method (e.g., centrifugal tumbling granulation, etc.), fluid-bed granulation (e.g., tumbling fluid-bed granulation, fluidized granulation, etc.), stirring granulation and the like. Among others, preferred is fluid-bed granulation method, more preferred is tumbling fluid-bed granulation method.

Concrete example of the "tumbling granulation method" includes a method using "CF apparatus" manufactured by Freund Industrial Co., Ltd. and the like. Concrete examples of the "tumbling fluid-bed granulation method" include methods using "SPIR-A-FLOW", "multi plex" manufactured by Powrex Corp., "New-Marumerizer" manufactured by Fuji Paudal Co., Ltd., and the like. The method for spraying the mixed liquid mentioned below can be suitably selected in accordance with the kind of granulator, and may be, for example, any one of a top spray method, a bottom spray method, a tangential spray method, and the like. Among others, a tangential spray method is preferred.

The "composition containing PPI" is produced by, for example, coating a core containing microcrystalline cellulose and lactose with PPI.

For example, employed is a method described in JP-A-5-92918 (coating method), which comprises coating a core comprising microcrystalline cellulose and lactose with PPI, if necessary together with a basic inorganic salt, binders, lubricants, diluents, a water-soluble polymer, etc. (hereinafter, may be abbreviated to "coating layer"). For example, employed is a method which comprises coating a core with PPI and a basic inorganic salt, and then further with binders, lubricants, diluents, a water-soluble polymer, etc.

The average particle size of the "cores" is about 250 μm or less, preferably about 50 to about 250 μm, more preferably about 100 to about 250 μm, especially preferably about 100 to about 200 μm. The "cores" having the above average particle size include particles which all pass through a sieve No. 50 sieve (300 μm), particles where about 5 w/w % or less of the total remain on a sieve No. 60 sieve (250 μm), and particles where about 10 w/w % or less of the total pass through a sieve No. 282 sieve (53 μm). The specific volume of the "core" is about 5 ml/g or less, preferably about 3 ml/g or less.

Examples of the "core" include (1) a spherical granulated product comprising microcrystalline cellulose and lactose, (2) a spherical granulated product being about 150 to about 250 μm and comprising microcrystalline cellulose (Avicel SP, manufactured by Asahi Chemical Co., Ltd.), (3) a stirring granulated product being about 50 to about 250 μm and comprising lactose (9 parts) and pregelatinized starch (1 part), (4) a micro particle being about 250 μm or less classified as a spherical granule composed of microcrystalline cellulose described in JP-A-61-213201, (5) a processed product such as wax formed to a sphere by spray chilling or melting granulation, (6) a processed product such as gelatin beads comprising oil component, (7) calcium silicate, (8) starch, (9) a porous particle such as chitin, cellulose, chitosan, etc, and (10) a bulk product such as granulated sugar, crystalline lactose, microcrystalline cellulose or sodium chloride, and processed preparations thereof. Further, these cores may be produced in accordance with per se known grinding method or granulation method, and sifted to prepare the particles having the desired particle size.

The above "spherical granulated product comprising microcrystalline cellulose and lactose" includes, for example, (i) a spherical granulated product being about 100 to about 200 μm and comprising microcrystalline cellulose (3 parts) and lactose (7 parts) [e.g., Nonpareil 105 (70-140) (particle size of about 100 to about 200 μm), manufactured by Freund Industrial Co., Ltd.], (ii) a spherical granulated product being about 150 to about 250 μm and comprising microcrystalline cellulose (3 parts) and lactose (7 parts) [e.g., Nonpareil NP-7:3, manufactured by Freund Industrial Co., Ltd.], (iii) a spherical granulated product being about 100 to about 200 μm and comprising microcrystalline cellulose (4.5 parts) and lactose (5.5 parts) [e.g., Nonpareil 105T (70-140) (particle size of about 100 to about 200 μm), manufactured by Freund Industrial Co., Ltd.], (iv) a spherical granulated product being about 150 to about 250 μm and comprising microcrystalline cellulose (5 parts) and lactose (5 parts) [e.g., Nonpareil NP-5:5, manufactured by Freund Industrial Co., Ltd.], and the like.

In order to produce a pharmaceutical preparation which is superior in dissolution while retaining suitable strength, the "core" includes, for example, preferably the spherical granulated product comprising microcrystalline cellulose and lactose, more preferably the spherical granulated material comprising microcrystalline cellulose and lactose and containing 50 wt % or more of lactose. Among others, preferred is a core comprising 40 to 50 wt % of microcrystalline cellulose and 50 to 60 wt % of lactose.

The "core" employed in the present invention is preferably the spherical granulated product comprising microcrystalline cellulose and lactose, more preferably the spherical granulated product being about 100 to about 200 µm and comprising microcrystalline cellulose (4.5 parts) and lactose (5.5 parts).

The "core" may contain PPI. Even when the core does not contain PPI, the releaseability of PPI can be controlled by a coating layer containing PPI.

The "core" is preferably as uniform a sphere as possible, for reducing the irregularity of the coating, in addition to being a powdery core.

The ratio of the "coating layer" to the "core" can be selected within the range in which it is possible to control dissolution of PPI and particle size of the composition, for example, generally about 50 to about 400 parts by weight per 100 parts by weight of the core.

The "coating layer" may be constructed by plural layers. At least one layer of the plural layers must contain PPI. The combination of various layers such as a coating layer not containing the active ingredient, a base coating layer, and an enteric coating layer which constitute the coating layer can be suitably selected.

When the "core" is coated, for example, PPI and the water-soluble polymer can be used as a mixed liquid. The liquid may be a solution or a dispersion, and can be prepared by using an organic solvent such as water or ethanol or an admixture thereof.

The concentration of the water-soluble polymer in the liquid varies according to the ratio of PPI and the additives, and is generally about 0.1 to about 50 wt %, preferably about 0.5 to about 10 wt %, in order to retain the binding strength of PPI to the core and maintain the viscosity of the liquid so as not to reduce the workability.

Where the coating layer comprises plural layers, the concentration of PPI in each layer may be changed successively or gradually by selecting for the content ratio or viscosity of the water-soluble polymer or by successive coating with mixed liquid varying in the ratio of PPI and the other additives. In the above case, it may be coated with a mixed liquid in which the content ratio of the water-soluble polymer is out of the range of about 0.1 to about 50 wt %, as long as the coating layer as a whole contains about 0.1 to about 50 wt % of the water-soluble polymer. Further, in forming the inactive coat according to known methods, the coating layer may comprise some layers such that the inactive layer may block each layer containing PPI.

The above-mentioned coated product is dried and sieved to give a composition having a uniform particle size. Since the shape of the composition generally corresponds to the core, an about spherical composition can also be obtained. As the sieve, for example, No. 50 (300 µm) round sieve can be used, and the composition is obtained by passing the product through the No. 50 round sieve.

The "enteric micro granules containing PPI" can be produced according to a granulation method similar to the above, for example, a method which comprises coating the composition with an enteric coating layer, in order to protect PPI or to impart enteric dissolution. If necessary, the composition containing PPI coated with an enteric coating layer may be further coated by a water-soluble sugar alcohol, preferably mannitol. In such case, the strength of the dry coated tablet comprising micro granules is improved.

The "enteric coating layer" is preferably a layer having about 20 to about 70 µm, more preferably about 30 to about 50 µm of thickness and coating the whole surface of the composition containing PPI. Accordingly, the smaller particle size of the composition, the higher the wt % of the enteric coating layer in the whole micro granule. In the "enteric micro granules containing PPI", the "enteric coating layer" is generally about 30 to about 70 wt %, preferably about 50 to about 70 wt %, of the micro granule as a whole.

The "enteric coating layer" may be constructed by plural (e.g., 2 or 3) layers. For example, employed is a method which comprises coating a composition with an enteric coating layer having polyethyleneglycol, and then with an enteric coating layer having triethyl citrate. For example, employed is a method which comprises coating a composition with an enteric coating layer having polyethyleneglycol, and then with an enteric coating layer having triethyl citrate, followed by being coated with an enteric coating layer having polyethyleneglycol.

(2)-3: "Outer Layer"

The "outer layer" in the dry coated tablet of the present invention is a part constituting the outside of the inner core, and contains 1) "enteric micro granules containing PPI" and 2) an additive. The additive is a component of the outer layer and contained in a part other than the "enteric micro granules containing PPI".

The dry coated tablet of the present invention is also obtained by mixing "enteric micro granules containing PPI", "an enteric-coated tablet containing acetylsalicylic acid" and an additive by a method known per se and tableting the mixture. To ensure sufficient tablet strength, and improve acid resistance, preferably, "enteric micro granules containing PPI" and an diluent are mixed and then granulated (when desired, a binder is sprayed for granulation) to give an outer layer granulated powder, which is then mixed with an outer layer mixture component such as other diluent and the like to give an outer layer mixed powder. This outer layer mixed powder is tableted together with "an enteric-coated tablet containing acetylsalicylic acid", whereby the dry coated tablet of the present invention is obtained.

The content of the "enteric micro granules containing PPI" is generally about 30-about 70 wt %, preferably about 30-about 60 wt %, of the "outer layer".

As the aforementioned "additive", one or more, preferably 1-5 kinds from diluent such as water-soluble sugar alcohol, microcrystalline cellulose, magnesium alumino metasilicate and the like, disintegrant and the like are used, and further, binder, corrigent, artificial sweetener, flavor, lubricant, colorant, stabilizer and the like are also used.

Examples of the aforementioned "diluent" include those mentioned above and, for example, lactose, sucrose, starch, cornstarch, light anhydrous silicic acid and the like.

The aforementioned "water-soluble sugar alcohol" means sugar alcohol that requires less than 30 ml of water to dissolve 1 g of sugar alcohol in water by vigorously shaking them for 30 seconds at 20° C. at 5 min intervals for about 30 min.

Examples of the "water-soluble sugar alcohol" include sorbitol, mannitol, maltitol, reduced starch saccharides, xylitol, reduced paratinose, erythritol and the like. Two or more kinds (preferably 2-3 kinds) thereof may be mixed at an appropriate ratio and used.

The "water-soluble sugar alcohol" is preferably mannitol, xylitol, erythritol, more preferably mannitol, erythritol, and particularly preferably mannitol (particularly D-mannitol). As erythritol, one generally produced from glucose as a starting material by fermentation by yeast and the like, which has a particle size of 50 mesh or below, is used. Erythritol may be a commercially available product (Nikken Chemicals Co., Ltd. etc.).

The aforementioned "microcrystalline cellulose" may be any as long as it is obtained by partially depolymerizing α-cellulose, followed by purification. It also includes those called microcrystalline cellulose. Specific examples of microcrystalline cellulose include CEOLUS KG802, CEOLUS KG1000, Avicel PH101, Avicel PH102, Avicel PH301, Avicel PH302, Avicel RC-591 (microcrystalline cellulose-carmellose sodium) (all manufactured by Asahi Kasei Chemicals Co., Ltd.) and the like. Preferred is CEOLUS KG1000. Such microcrystalline cellulose may be used alone or two or more kinds (preferably 2-3 kinds) thereof may also be used in combination.

Specific examples of the aforementioned "magnesium alumino metasilicate" include Neusilin FH1, Neusilin FL1, Neusilin NFL2N, Neusilin UFL2 (all manufactured by Fuji Chemical Industry Co., Ltd.) and the like. Preferred is Neusilin UFL2. Such magnesium alumino metasilicate may be used alone or two or more kinds (preferably 2-3 kinds) thereof may also be used in combination.

In the present invention, to improve the strength of the dry coated tablet, at least one kind selected from microcrystalline cellulose and magnesium alumino metasilicate is preferably added to the "outer layer".

The content of the aforementioned "water-soluble sugar alcohol" in the "outer layer" is generally about 10-about 60 wt %.

The content of the aforementioned "microcrystalline cellulose" in the "outer layer" is generally about 5-about 40 wt %.

The content of the aforementioned "magnesium alumino metasilicate" in the "outer layer" is generally about 1-about 10 wt %.

The content of the aforementioned "diluent" in the "outer layer" is generally about 15-about 80 wt %.

As the aforementioned "disintegrant", those conventionally used in the pharmaceutical field can be used. For example, (1) crospovidone (e.g., Kollidon CL-F (manufactured by BASF)), (2) a disintegrant referred to as superdisintegrant such as croscarmellose sodium (FMC-Asahi Kasei), carmellose calcium (GOTOKU CHEMICAL CO., LTD.) and the like, (3) sodium carboxymethyl starch (e.g., manufactured by Matsutani Chemical Industry Co., Ltd.), (4) low-substituted hydroxypropylcellulose (e.g., manufactured by Shin-Etsu Chemical Co., Ltd.), (5) cornstarch and the like can be mentioned.

The "crospovidone" may be any of polyvinylpolypyrrolidone (PVPP), those referred to as 1-vinyl-2-pyrrolidinone homopolymer, a crosslinked polymer substance having a chemical name of 1-ethenyl-2-pyrrolidinone homopolymer. Specific examples include Kollidon CL (manufactured by BASF), Kollidon CL-F (manufactured by BASF), Polyplasdone XL (manufactured by ISP), Polyplasdone XL-10 (manufactured by ISP), Polyplasdone INF-10 (manufactured by ISP) and the like. The content of the aforementioned "disintegrant" in the "outer layer" is generally about 1-about 15 wt %.

Examples of the aforementioned "binder" include hydroxypropylcellulose, hydroxypropylmethylcellulose, microcrystalline cellulose, pregelatinized starch, polyvinylpyrrolidone, gum arabic powder, gelatin, pullulan, low-substituted hydroxypropylcellulose and the like. The content of the aforementioned "binder" in the "outer layer" is generally about 1-about 15 wt %. Examples of the aforementioned "corrigent" include citric acid (citric anhydride), tartaric acid, malic acid and the like.

Examples of the aforementioned "artificial sweetener" include saccharin sodium, dipotassium glycyrrhetinate, aspartame, stevia, thaumatin and the like.

The aforementioned "flavor" may be any of a synthetic substance and a naturally occurring substance and, for example, lemon, lime, orange, menthol, strawberry and the like can be mentioned.

Examples of the aforementioned "lubricant" include magnesium stearate, sucrose ester of fatty acid, glycerol fatty acid ester, polyethylene glycol, talc, stearic acid, hydrogenated oil and the like. The content of the aforementioned "lubricant" in the "outer layer" is generally about 0.1-about 3 wt %.

Examples of the aforementioned "colorant" include food colors such as Food Color Yellow No. 5, Food Color Red No. 2, Food Color Blue No. 2 and the like; food lake colors, yellow ferric oxide, red ferric oxide and the like.

As the aforementioned "stabilizer", the aforementioned basic inorganic salt and the like can be mentioned.

A preferable embodiment of the "outer layer" in the present invention is a layer containing 1) granules obtained by mixing "enteric micro granules containing PPI" and a diluent (e.g., water-soluble sugar alcohol such as sorbitol, mannitol, maltitol, reduced starch saccharides, xylitol, reduced paratinose, erythritol and the like; microcrystalline cellulose and the like, particularly D-mannitol and microcrystalline cellulose), and granulating the mixture using, when desired, a binder (e.g., hydroxypropylcellulose, hydroxypropylmethylcellulose, microcrystalline cellulose, pregelatinized starch, polyvinylpyrrolidone, gum arabic powder, gelatin, pullulan, low-substituted hydroxypropylcellulose etc., particularly hydroxypropylcellulose) and the like (hereinafter sometimes to be referred to as "outer layer granulated powder"), and 2) optionally added various additives such as diluent (e.g., at least 1 kind selected from microcrystalline cellulose and magnesium alumino metasilicate), disintegrant (e.g., crospovidone), lubricant and the like (hereinafter sometimes to be referred to as "outer layer mixture component").

Where necessary, the above-mentioned outer layer mixture component may further contain an additive such as the aforementioned water-soluble sugar alcohol, binder, corrigent, artificial sweetener, flavor, lubricant, colorant, stabilizer and the like as appropriate.

The content of water-soluble sugar alcohol in the aforementioned "outer layer granulated powder" is generally about 10-about 95 parts by weight, preferably about 50-about 95 parts by weight, per 100 parts by weight of the component other than the "enteric micro granules containing PPI" in the outer layer.

The content of microcrystalline cellulose in the aforementioned "outer layer granulated powder" is generally about 1-about 50 parts by weight, preferably about 5-about 25 parts by weight, per 100 parts by weight of the component other than the "enteric micro granules containing PPI" in the outer layer.

The content of the binder used as necessary for granulation of the aforementioned "outer layer granulated powder"

is generally about 0.1-about 20 parts by weight, preferably about 1-about 15 parts by weight, per 100 parts by weight of the component other than the "enteric micro granules containing PPI" in the outer layer.

The "outer layer containing enteric micro granules containing PPI" is preferably formed to surround the inner core by mixing the aforementioned outer layer granulated powder and an outer layer mixture component, and tableting the mixture together with the inner core.

The content of the diluent such as microcrystalline cellulose, magnesium alumino metasilicate and the like in the outer layer mixture component is generally about 30-about 80 parts by weight, preferably about 50-about 75 parts by weight, per 100 parts by weight of the outer layer mixture component.

The content of magnesium alumino metasilicate in the outer layer mixture component is generally about 5-about 40 parts by weight, preferably about 10-about 30 parts by weight, per 100 parts by weight of the outer layer mixture component.

The content of the disintegrant such as crospovidone and the like in the outer layer mixture component is generally about 1-about 35 parts by weight, preferably about 5-about 35 parts by weight, per 100 parts by weight of the outer layer mixture component.

The content of the lubricant such as magnesium stearate and the like in the outer layer mixture component is generally about 0.01-about 20 parts by weight, preferably about 1-about 10 parts by weight, per 100 parts by weight of the outer layer mixture component.

The "mixing" in the production step of the "outer layer containing enteric micro granules containing PPI" is performed by a general mixing method. The "mixing" is performed using an apparatus, for example, vertical granulator VG10 (manufactured by POWREX CORPORATION), fluid-bed granulator LAB-1, FD-3S, FD-WSG-60 (all manufactured by POWREX CORPORATION), FLO-5M (manufactured by FREUND), V-type mixer, tumbler mixer and the like.

For the production of the outer layer granulated powder, a granulation method such as a tumbling granulation method (e.g., centrifugation tumbling granulation method), a fluid-bed granulation method, a stirring granulation method and the like is used. Particularly preferred is a fluid-bed granulation method.

(3) Dry Coated Tablet

The tablet weight of the dry coated tablet of the present invention is generally about 350 mg-about 550 mg. The weight ratio of the "enteric-coated tablet containing acetylsalicylic acid" (inner core) and the "outer layer containing enteric micro granules containing PPI" is desirably about 1:2-about 1:6, preferably about 1:2-about 1:4, to maintain the physical strength of the tablet.

The "dry coated tablet" of the present invention is produced by a method conventionally used in the pharmaceutical field.

As mentioned above, the dry coated tablet of the present invention is obtained by mixing "enteric micro granules containing PPI" and "an optionally added additive" by a method known per se, and tableting the mixture together with "an enteric-coated tablet containing acetylsalicylic acid". Particularly, it is preferable to granulate a mixture of "enteric micro granules containing PPI" and a diluent to give an outer layer granulated powder, mix the resulting powder with other outer layer mixture component such as diluent and the like to give an outer layer mixed powder, and tablet the outer layer mixed powder together with "an enteric-coated tablet containing acetylsalicylic acid".

The "tableting" of the dry coated tablet is performed by punching at a pressure of 1-40 kN/cm$^2$, 5-30 kN/cm$^2$, preferably 10-30 kN/cm$^2$, by single punch tableting using Autograph (manufactured by Shimadzu Corporation) or rotary dry coating tableting machine (manufactured by Kikusui Seisakusho Ltd. or HATA IRON WORKS CO., LTD.) and the like. When using a rotary tableting machine, tableting is performed at general rotation, for example, 3-40 min$^{-1}$, preferably 3-30 min$^{-1}$, more preferably 8-25 min$^{-1}$.

The tablet size of the preparation is desirably a diameter of 5.0-8.0 mm for the inner core tablet (plain tablet), and a diameter of 8.0-11.0 mm for the dry coated tablet. The difference in the diameter between the inner core tablet (plain tablet) and the dry coated tablet is desirably not less than 2.0 mm to ensure the tablet strength of the dry coated tablet. Here, the "tablet size" means a diameter of a round tablet or a shorter diameter of an ellipse tablet. The diameter of the inner core tablet (plain tablet) is a diameter of the plain tablet without coating with an "enteric coating component", namely, a diameter before coating with an "enteric coating component".

It is important for the maintenance of the physical strength to ensure a certain level of difference in the size of the inner core tablet (plain tablet) and the outer layer of the dry coated tablet of the present invention.

After tableting, "drying" may be applied where necessary. The drying may be performed by any method generally used for drying preparations, such as vacuum drying, fluid-bed drying and the like.

The tableting step of the dry coated tablet of the present invention may be performed at room temperature or a temperature above room temperature.

The "room temperature" refers to a temperature of the room where tableting is performed for general production of tablets, which is generally about 20° C.-about 23° C. That is, the "temperature above room temperature" refers to a temperature exceeding this temperature, where the lower limit is preferably about 25° C. While the temperature varies depending on the starting material powder, granule and the like to be used, it is generally preferably about 25° C.-about 50° C. The temperature can be changed according to the quality of the desired tablet.

The dry coated tablet of the present invention may be a plain tablet or a film-coated agent, with preference given to a plain tablet. In the present specification, the "plain tablet" means a tablet free of a coating treatment such as film coating and the like on the surface of the dry coated tablet obtained in the tableting step.

In addition, the dry coated tablet of the present invention has an appropriate hardness that prevents damage in a preparation step or a distribution process. The tablet strength (value measured by a tablet hardness meter) is generally about 40-about 200 N, more preferably about 60-about 150 N.

The dry coated tablet of the present invention has a friability of generally not more than 1%, preferably not more than 0.5%.

The dry coated tablet of the present invention can show an acid resistance rate of both acetylsalicylic acid and proton pump inhibitor of not more than 10%, preferably not more than 8%, more preferably not more than 5%.

Since the dry coated tablet of the present invention contains PPI, it has superior antiulcer activity, gastric acid secretion-inhibitory action, mucosa-protecting action, anti-*Helicobacter pylori* activity and the like.

On the other hand, since the dry coated tablet of the present invention contains acetylsalicylic acid, it is useful as a prophylactic and/or therapeutic agent for diseases of cerebrovascular or circulatory, for example, a thrombus and/or embolization inhibitor for angina pectoris (chronic stable angina pectoris, unstable angina pectoris), myocardial infarction; a prophylactic and/or therapeutic agent for ischemic cerebrovascular disorder (transient ischemic attack (TIA), cerebral infarction); a thrombus and/or embolization inhibitor used after coronary-artery bypass surgery (CABG) or percutaneous transluminal coronary angioplasty (PTCA); or a prophylactic and/or therapeutic agent for Kawasaki disease (including cardiovascular sequelae due to Kawasaki disease). Therefore, the dry coated tablet of the present invention can be administered for the treatment or suppression of the onset of gastric ulcer or duodenal ulcer while continuing administration of acetylsalicylic acid. When prophylaxis and/or treatment of such diseases is desired, about 10 mg-about 40 mg of PPI is administered per one day, and a low dose of about 70 mg-about 120 mg of acetylsalicylic acid is administered per one day.

Moreover, acetylsalicylic acid can also be used as one kind of non-steroidal anti-inflammatory drug for the treatment of mainly pain, fever and inflammation. non-steroidal anti-inflammatory drug may cause gastric ulcer or duodenal ulcer. Particularly, in the treatment of rheumatoid arthritis, osteoarthritis and the like, discontinuation of administration of non-steroidal anti-inflammatory drug may be difficult, since it markedly degrades the QOL. In such cases, the dry coated tablet of the present invention can be administered for the treatment or suppression of the onset of gastric ulcer or duodenal ulcer while continuing administration of a non-steroidal anti-inflammatory drug.

When such treatment is desired, about 10 mg-about 40 mg of PPI is administered per one day, and about 240 mg-about 400 mg of acetylsalicylic acid is administered per one day.

Therefore, such dry coated tablet of the present invention is useful as a low toxic and safe combination drug of PPI and acetylsalicylic acid.

The dry coated tablet of the present invention can be orally administered to a mammal (e.g., human, monkey, sheep, horse, dog, cat, rabbit, rat, mouse and the like) for suppression of thrombus and/or embolization in cerebrovascular or circulatory diseases, treatment or prophylaxis of ulcer caused by non-steroidal anti-inflammatory agent; and the like.

In addition to the above-mentioned objects, for eradication or aid of eradication of *Helicobacter pylori*, the dry coated tablet of the present invention may be used in combination with a penicillin antibiotic (e.g., amoxicillin and the like) and an erythromycin antibiotic (e.g., clarithromycin and the like).

The daily dose of the dry coated tablet of the present invention varies depending on the severity of symptom, the age, sex and body weight of the subject of administration, the timing and interval of administration, the kind of the active ingredient and the like, and is not particularly limited. The dry coated tablet of the present invention may be administered once a day or in 2 or 3 portions a day.

In addition, the present invention also relates to a production method of a dry coated tablet comprising mixing enteric micro granules containing PPI with a diluent, granulating the mixture and tableting the obtained granules together with an enteric-coated tablet containing acetylsalicylic acid and an optionally added additive.

The "enteric micro granules containing PPI", "diluent", "enteric-coated tablet containing acetylsalicylic acid", "optionally added additive", mixing, granulation, tableting method and the like are the same as those explained above regarding the above-mentioned dry coated tablet of the present invention.

A dry coated tablet produced by the production method of the present invention is superior in tablet strength, and dissolution property, preservation stability and acid resistance of the active ingredients (acetylsalicylic acid and PPI).

Since dry coated tablet has a double structure of an inner core and an outer layer, it generally has a problem of weak binding force between the inner core and the outer layer. In addition, a dry coated tablet containing "enteric micro granules containing PPI", which are functional micro granules having a large average particle size, in an outer layer has a problem of a weaker binding force between the inner core and the outer layer. A dry coated tablet produced by the production method of the present invention has solved such problem and has superior tablet strength.

In general, a dry coated tablet can be obtained by compression molding an outer layer mixed powder and an inner core tablet. Since a large pressure is applied in compression molding, the enteric coating layer of the inner core tablet and the enteric coating layer of the "enteric micro granules containing PPI" contained in the outer layer mixed powder are easily broken. Therefore, a sufficient acid resistance rate while maintaining sufficient tablet strength cannot be ensured with ease. A dry coated tablet produced by the production method of the present invention solves this problem and simultaneously maintains sufficient tablet strength and superior acid resistance.

A dry coated tablet produced by the production method of the present invention has an appropriate hardness that prevents damage in a preparation step or a distribution process. The tablet strength (value measured by a tablet hardness meter) is generally about 40-about 200 N, more preferably about 60-about 150 N.

The dry coated tablet of the present invention has a friability of generally not more than 1%, preferably not more than 0.5%.

The dry coated tablet of the present invention can show an acid resistance rate of both acetylsalicylic acid and proton pump inhibitor of not more than 10%, preferably not more than 8%, more preferably not more than 5%.

EXAMPLES

The present invention is explained in more detail in the following by referring to Reference Example, Examples, Comparative Examples and evaluation (Experimental Examples), which are not to be construed as limitative.

The acid resistance rate in the present specification is obtained by a dissolution test by The Japanese Pharmacopoeia Dissolution Test Method 2 using 0.1N HCl 500 mL (75 rpm) for 1 hr, after which the test solution was collected, filtered through a 0.45 μm membrane filter, the absorbance was measured and the dissolution ratio of the drug in 0.1N HCl was calculated.

The hardness value was measured by a tablet hardness meter.

The friability means a value measured by the Japanese Pharmacopoeia, "test method of tablet friability".

The compositions of the dry coated tablets shown in the below-mentioned Examples 1, 2 and 6-14 are shown in Table 1. The compositions of the dry coated tablets shown in the below-mentioned Examples 3-5 are shown in Table 2.

TABLE 1

| component name | Example 1 formulation amount (mg per tablet) | Examples 2 and 6-14 formulation amount (mg per tablet) |
| --- | --- | --- |
| acetylsalicylic acid (Rhodine 3118) | 100.0 | 100.0 |
| cornstarch | 11.0 | 11.0 |
| microcrystalline cellulose (KG-1000) | 6.5 | |
| microcrystalline cellulose (PH-101) | | 6.5 |
| carmellose | 6.5 | 6.5 |
| methacrylic acid copolymer LD (solid content) (Eudragit L30D-55) | 9.11 | 9.11 |
| ethyl acrylate-methyl methacrylate copolymer (solid content) (Eudragit NE30D) | 1.01 | 1.01 |
| polysorbate 80 | 0.24 | 0.24 |
| glycerol monostearate | 0.61 | 0.61 |
| citric anhydride | 0.01 | 0.01 |
| triethyl citrate | 2.02 | 2.02 |
| inner core tablet subtotal (mg) | 137.0 | 137.0 |
| lansoprazole enteric micro granules | 135 | 135 |
| D-mannitol | 86.0 | 86.0 |
| microcrystalline cellulose (KG-1000) | 9.5 | 9.5 |
| hydroxypropylcellulose | 9.3 | 9.3 |
| crospovidone | 15 | 15 |
| microcrystalline cellulose (KG-1000) | 31.4 | 31.4 |
| magnesium alumino metasilicate (Neusilin UFL2) | 9.0 | 9.0 |
| magnesium stearate | 4.8 | 4.8 |
| outer layer component subtotal (mg) | 300.0 | 300.0 |
| dry coated tablet total (mg) | 437.0 | 437.0 |

TABLE 2

| component name | Example 3 formulation amount (mg per tablet) | Example 4 formulation amount (mg per tablet) | Example 5 formulation amount (mg per tablet) |
| --- | --- | --- | --- |
| acetylsalicylic acid (Rhodine 3118) | 100.0 | 100.0 | 100.0 |
| cornstarch | 11.0 | 11.0 | 11.0 |
| microcrystalline cellulose (PH-101) | 6.5 | 6.5 | 6.5 |
| carmellose | 6.5 | 6.5 | 6.5 |
| methacrylic acid copolymer LD (solid content) (Eudragit L30D-55) | 18.22 | 7.01 | 8.10 |
| ethyl acrylate-methyl methacrylate copolymer (solid content) (Eudragit NE30D) | 2.02 | 0.78 | 2.02 |
| polysorbate 80 | 0.48 | 0.18 | 0.24 |
| glycerol monostearate | 1.22 | 0.47 | 0.61 |
| citric anhydride | 0.02 | 0.008 | 0.02 |
| triethyl citrate | 4.04 | 1.55 | 2.02 |
| inner core tablet subtotal (mg) | 150 | 134.0 | 137.0 |
| lansoprazole enteric micro granules | 135 | 135 | 135 |
| D-mannitol | 86.0 | 86.0 | 86.0 |
| micro crystalline cellulose (KG-1000) | 9.5 | 9.5 | 9.5 |
| hydroxypropylcellulose | 9.3 | 9.3 | 9.3 |
| crospovidone | 15 | 15 | 15 |
| micro crystalline cellulose (KG-1000) | 31.4 | 31.4 | 31.4 |
| magnesium alumino metasilicate (Neusilin UFL2) | 9.0 | 9.0 | 9.0 |
| magnesium stearate | 4.8 | 4.8 | 4.8 |
| subtotal of outer layer components (mg) | 300.0 | 300.0 | 300.0 |
| dry coated tablet total (mg) | 450.0 | 434.0 | 437.0 |

Reference Example 1

Production of Lansoprazole Enteric Micro Granules Lansoprazole-Containing Micro Granules Nonpareil 105 (trade name 41.6 kg) was charged in a tumbling fluid-bed coating granulator (POWREX CORPORATION, MP-400), and a lansoprazole-containing coating solution prepared in advance, which had the following composition, was sprayed for coating. Furthermore, an intermediate layer coating solution prepared in advance, which had the following composition, was sprayed for coating. After completion of the coating, the granules were dried to give lansoprazole-containing micro granules (132 kg).

[Lansoprazole-Containing Coating Solution]

| | |
| --- | --- |
| lansoprazole | 39.60 kg |
| magnesium carbonate | 13.20 kg |
| low-substituted hydroxypropylcellulose | 6.60 kg |
| hydroxypropylcellulose | 13.20 kg |
| (purified water) | (185 L) |

[Intermediate Layer Coating Solution]

| | |
| --- | --- |
| hydroxypropylmethylcellulose | 9.24 kg |
| low-substituted hydroxypropylcellulose | 6.60 kg |
| sterile talc | 3.96 kg |
| titanium oxide | 3.96 kg |
| mannitol | 9.24 kg |
| (purified water) | (99.0 L) |

Lansoprazole Enteric Micro Granules

A lansoprazole-containing micro granules (44.0 kg) was charged in a tumbling fluid-bed coating granulator (manufactured by POWREX CORPORATION, MP-400), enteric coating solution 1 prepared in advance, which had the following composition, enteric coating solution 2 prepared in advance, which had the following composition, and an overcoating solution were sprayed for coating. After completion of the coating, drying was performed to give lansoprazole enteric micro granules (about 110 kg) were obtained.

[Glycerol Monostearate Solution]

| | |
| --- | --- |
| glycerol monostearate | 3.150 kg |
| polysorbate 80 | 0.945 kg |
| yellow ferric oxide | 0.0315 kg |
| red ferric oxide | 0.0315 kg |
| (purified water) | (63 L) |

[Enteric Coating Solution 1]

| Eudragit L30D-55 | 9.615 kg solid amount |
| --- | --- |
| | (32.05 kg) (liquid amount) |
| Eudragit NE30D | 1.071 kg solid amount |
| | (3.570 kg) (liquid amount) |
| polyethylene glycol 6000 | 1.071 kg |
| citric anhydride | 0.0126 kg |
| (purified water) | (31.8 L) |
| glycerol monostearate solution | 13.4 kg (liquid amount) |

[Enteric Coating Solution 2]

| Eudragit L30D-55 | 35.28 kg solid amount |
| --- | --- |
| | (117.6 kg) (liquid amount) |
| Eudragit NE30D | 3.918 kg solid amount |
| | (13.06 kg) (liquid amount) |
| triethyl citrate | 7.854 kg |
| citric anhydride | 0.021 kg |
| (purified water) | (9.33 L) |
| glycerol monostearate solution | 53.7 kg (liquid amount) |

[Overcoating Solution]

| mannitol | 4.200 kg |
| --- | --- |
| (purified water) | (25.2 L) |

Example 1

Acetylsalicylic acid (granulation product: manufactured by Rhodia, Rhodine 3118, 57000 g), cornstarch (6270 g), microcrystalline cellulose (CEOLUS KG-1000 (trade name; manufactured by Asahi Kasei Chemicals Co., Ltd.), 3705 g) and carmellose (3705 g) were measured and mixed in a tumbler mixer. This was tableted using a rotary tableting machine (manufactured by Kikusui Seisakusho Ltd.) and φ7.0 mm R round punch to give a plain tablet (tablet weight 124 mg) of the inner core. 20% aqueous polysorbate 80 solution (960 g) was dissolved in water (21940 g), heated to 70° C., and glycerol monostearate (488 g) was dispersed in a dispersion machine to give a glycerol monostearate dispersion. Thereto were added methacrylic acid copolymer LD (Eudragit L30D-55 (trade name; manufactured by EVONIK INDUSTRIES), 24290 g (solid amount 7287 g)), ethyl acrylate-methyl methacrylate copolymer (Eudragit NE30D (trade name; manufactured by EVONIK INDUSTRIES), 2696 g (solid amount 808.8 g), citric anhydride (8 g) and triethyl citrate (1616 g) and mixed to give an enteric coating solution. Using a dria coater (manufactured by POWREX CORPORATION), the aforementioned plain tablet (60760 g) was coated with the enteric coating solution such that the solid component of the enteric coating was 13 mg per tablet to give an inner core tablet (tablet weight 137 mg).

Lansoprazole enteric micro granules (37800 g), D-mannitol (24080 g) and microcrystalline cellulose (2660 g) were measured, and the mixture was granulated in a fluid-bed granulator (POWREX CORPORATION, FD-WSG-60) while spraying 6% hydroxypropylcellulose solution (43400 g) to give a granulated powder. Crospovidone (3750 g), microcrystalline cellulose (CEOLUS KG-1000 (trade name; manufactured by Asahi Kasei Chemicals Co., Ltd.), 7850 g), magnesium alumino metasilicate (Neusilin UFL2 (trade name; manufactured by Fuji Chemical Industry Co., Ltd.), 2250 g), magnesium stearate (1200 g) and the aforementioned granulated powder (59950 g) were mixed in a tumbler mixer to give an outer layer mixed powder.

The inner core tablet (32880 g) and outer layer mixed powder (72000 g) were subjected to dry coating tableting (rotation 15 rpm, tableting pressure 21 kN) using an R punch having a diameter of 10 mm in a rotary dry coating tableting machine (manufactured by HATA IRON WORKS CO., LTD.) to give a dry coated tablet with the tablet weight of 437 mg/tablet (weight constitution; inner core tablet 137 mg, outer layer 300 mg).

Example 2

Acetylsalicylic acid (granulation product: manufactured by Rhodia, Rhodine 3118, 57000 g), cornstarch (6270 g), microcrystalline cellulose (CEOLUS PH-101 (trade name; manufactured by Asahi Kasei Chemicals Co., Ltd.), 3705 g) and carmellose (3705 g) were measured and mixed in a tumbler mixer. This was tableted using a rotary tableting machine (manufactured by Kikusui Seisakusho Ltd.) and φ7.0 mm R round punch to give a plain tablet (tablet weight 124 mg) of the inner core. 20% aqueous polysorbate 80 solution (960 g) was dissolved in water (21940 g), heated to 70° C., and glycerol monostearate (488 g) was dispersed in a dispersion machine to give a glycerol monostearate dispersion. Thereto were added methacrylic acid copolymer LD (Eudragit L30D-55 (trade name; manufactured by EVONIK INDUSTRIES), 24290 g (solid amount 7287 g)), ethyl acrylate-methyl methacrylate copolymer (Eudragit NE30D (trade name; manufactured by EVONIK INDUSTRIES), 2696 g (solid amount 808.8 g), citric anhydride (8 g) and triethyl citrate (1616 g) and mixed to give an enteric coating solution. Using a dria coater (manufactured by POWREX CORPORATION), the aforementioned plain tablet (60760 g) was coated with the enteric coating solution such that the solid component of the enteric coating was 13 mg per tablet to give an inner core tablet (tablet weight 137 mg).

Lansoprazole enteric micro granules (37800 g), D-mannitol (24080 g) and microcrystalline cellulose (2660 g) were measured, and the mixture was granulated in a fluid-bed granulator (POWREX CORPORATION, FD-WSG-60) while spraying 6% hydroxypropylcellulose solution (43400 g) to give a granulated powder. Crospovidone (3750 g), microcrystalline cellulose (CEOLUS KG-1000 (trade name; manufactured by Asahi Kasei Chemicals Co., Ltd.), 7850 g), magnesium alumino metasilicate (Neusilin UFL2 (trade name; manufactured by Fuji Chemical Industry Co., Ltd.), 2250 g), magnesium stearate (1200 g) and the aforementioned granulated powder (59950 g) were mixed in a tumbler mixer to give an outer layer mixed powder.

The inner core tablet (32880 g) and outer layer mixed powder (72000 g) were subjected to dry coating tableting (rotation 15 rpm, tableting pressure 21 kN) using an R punch having a diameter of 10 mm in a rotary dry coating tableting machine (manufactured by HATA IRON WORKS CO., LTD.) to give a dry coated tablet with the tablet weight of 437 mg/tablet (weight constitution; inner core tablet 137 mg, outer layer 300 mg).

Example 3

Acetylsalicylic acid (granulation product: manufactured by Rhodia, Rhodine 3118, 57000 g), cornstarch (6270 g), microcrystalline cellulose (CEOLUS PH-101 (trade name; manufactured by Asahi Kasei Chemicals Co., Ltd.), 3705 g) and carmellose (3705 g) were measured and mixed in a tumbler mixer. This was tableted using a rotary tableting machine (manufactured by Kikusui Seisakusho Ltd.) and φ7.0 mm R round punch to give a plain tablet (tablet weight 124 mg) of the inner core. Polysorbate 80 (4.8 g) was dissolved in water (567.6 g), heated to 70° C., and glycerol monostearate (12.2 g) was dispersed in a dispersion machine to give a glycerol monostearate dispersion. Thereto were added methacrylic acid copolymer LD (Eudragit L30D-55 (trade name; manufactured by EVONIK INDUSTRIES), 607.4 g (solid amount 182.2 g)), ethyl acrylate-methyl methacrylate copolymer (Eudragit NE30D (trade name; manufactured by EVONIK INDUSTRIES), 67.4 g (solid amount 20.2 g), citric anhydride (0.2 g) and triethyl citrate (40.4 g) and mixed to give an enteric coating solution. Using a dria coater (manufactured by POWREX CORPORATION), the aforementioned plain tablet (248 g) was coated with the enteric coating solution such that the solid component of the enteric coating was 26 mg per tablet to give an inner core tablet (tablet weight 150 mg).

The inner core tablet obtained above and the outer layer mixed powder obtained in Example 2 were subjected to dry coating tableting (rotation 10 rpm, tableting pressure 15 kN) using an R punch having a diameter of 10 mm in a rotary dry coating tableting machine (manufactured by Kikusui Seisakusho Ltd.) to give a dry coating tablet with the tablet weight of 450 mg/tablet (weight constitution; inner core tablet 150 mg, outer layer 300 mg).

Example 4

Using a dria coater (manufactured by POWREX CORPORATION), the plain tablet of the inner core tablet (248 g) containing acetylsalicylic acid obtained by a method similar to that in Example 3 was coated with the enteric coating solution obtained by a method similar to that in Example 3, such that the solid component of the enteric coating was 10 mg per tablet to give an inner core tablet (tablet weight 134 mg).

The inner core tablet obtained above and the outer layer mixed powder obtained in Example 2 were subjected to dry coating tableting (rotation 10 rpm, tableting pressure 15 kN) using an R punch having a diameter of 10 mm in a rotary dry coating tableting machine (manufactured by Kikusui Seisakusho Ltd.) to give a dry coated tablet with the tablet weight of 434 mg/tablet (weight constitution; inner core tablet 134 mg, outer layer 300 mg).

Example 5

Polysorbate 80 (4.8 g) was dissolved in water (567.6 g), heated to 70° C., and glycerol monostearate (12.2 g) was dispersed in a dispersion machine to give a glycerol monostearate dispersion. Thereto were added methacrylic acid copolymer LD (Eudragit L30D-55 (trade name; manufactured by EVONIK INDUSTRIES), 540 g (solid amount 162 g)), ethyl acrylate-methyl methacrylate copolymer (Eudragit NE30D (trade name; manufactured by EVONIK INDUSTRIES), 134.6 g (solid amount 40.4 g)), citric anhydride (0.4 g) and triethyl citrate (40.4 g) and mixed to give an enteric coating solution. Using a dria coater (manufactured by POWREX CORPORATION), the plain tablet of the inner core tablet (248 g) containing acetylsalicylic acid obtained by a method similar to that in Example 3 was coated with the enteric coating solution such that the solid component of the enteric coating was 13 mg per tablet to give an inner core tablet (tablet weight 137 mg).

The inner core tablet obtained above and the outer layer mixed powder obtained in Example 2 were subjected to dry coating tableting (rotation 10 rpm, tableting pressure 15 kN) using an R punch having a diameter of 10 mm in a rotary dry coating tableting machine (manufactured by Kikusui Seisakusho Ltd.) to give a dry coated tablet with the tablet weight of 437 mg/tablet (weight constitution; inner core tablet 137 mg, outer layer 300 mg).

Example 6

Crospovidone (150 g), microcrystalline cellulose (CEOLUS KG-1000 (trade name; manufactured by Asahi Kasei Chemicals Co., Ltd.), 314 g), magnesium alumino metasilicate (Neusilin UFL2 (trade name; manufactured by Fuji Chemical Industry Co., Ltd.), 90 g), magnesium stearate (48 g) and the granulated powder (2398 g) obtained in Example 2 were mixed in a tumbler mixer to give an outer layer mixed powder.

The inner core tablet obtained in Example 2 and the outer layer mixed powder obtained above were subjected to dry coating tableting (rotation 10 rpm, tableting pressure 15 kN) using an R punch having a diameter of 10 mm in a rotary dry coating tableting machine (manufactured by HATA IRON WORKS CO., LTD.) to give a dry coated tablet with the tablet weight of 437 mg/tablet (weight constitution; inner core tablet 137 mg, outer layer 300 mg).

Evaluation

The evaluation results of the acid resistance rate, tablet strength and friability of the dry coated tablets obtained in Examples 1, 2 and 6 are shown in Table 3.

TABLE 3

Evaluation results of acid resistance rate and tablet strength in Examples

| | Example 1 | Example 2 | Example 6 |
|---|---|---|---|
| acid resistance rate (lansoprazole/acetylsalicylic acid) | 3%/0% | 2%/0% | not measured |
| hardness | 87N | 83N | 120N |
| friability | 0% | 0% | 0% |

Example 7

The acetylsalicylic acid mixed powder obtained in Example 2 was tableted in a rotary tableting machine (manufactured by Kikusui Seisakusho Ltd.) to give plain tablet 4 having the aforementioned grooves 6, 7. By using a punch (mold) having convex parts corresponding to grooves 6, 7 for tableting to form grooves 6, 7. The diameter of the plain tablet 4 was 7 mm and the weight was 124 mg. The opening width of the grooves 6, 7 was set to about 1 mm, depth to about 0.3 mm. Polysorbate 80 (4.8 g) was dissolved in water (567.6 g), heated to 70° C., and glycerol monostearate (12.2 g) was dispersed in a dispersion machine to give a glycerol monostearate dispersion. Thereto were added methacrylic acid copolymer LD (Eudragit L30D-55 (trade name; manufactured by EVONIK INDUSTRIES), 607.4 g (solid amount 182.2 g)), ethyl acrylate-methyl methacrylate copolymer (Eudragit NE30D (trade name; manufactured by EVONIK INDUSTRIES), 67.4 g (solid amount 20.2 g), citric anhydride (0.2 g) and triethyl citrate (40.4 g) and mixed to give an enteric coating solution.

Using a dria coater (manufactured by POWREX CORPORATION), the enteric coating solution was simultaneously applied to plural plain tablets 4 (total 620 g). The coating was performed until 13 mg of the solid component in the enteric coating solution attached to each plain tablet 4 to give inner core 2 (137 mg per tablet). The opening width and depth of grooves 8, 9 of the inner core 2 was almost equivalent to those of the grooves 6, 7 before coating, which were about 1 mm and about 0.3 mm, respectively.

The inner core 2 was covered with the outer layer mixed powder obtained in Example 2, and subjected to dry coating tableting to form outer layer 3. The outer diameter of the outer layer 3 was 10 mm and the weight was 437 mg (inner core 2: 137 mg, outer layer 3: 300 mg). For dry coating tableting, a rotary dry coating tableting machine (manufactured by Kikusui Seisakusho Ltd.) was used and the tableting pressure was 15 kN, and the rotation was 10 rpm. From the foregoing, the dry coated tablet of Example 7 was obtained. The smallest average particle size of the powdery solid component contained in the outer layer 3 was about 13 μm.

Example 8

In the same manner as in Example 7 except that the punch with which to form a plain tablet 4 had a different shape, inner core 2A having the aforementioned cross-like grooves 10A, 10B, 11A, 11B was obtained. The cross section of each groove was V-shaped, the opening width was about 1 mm and the depth was about 0.3 mm. Using the same enteric coating, the same mixed powder of outer layer 3, and the same other conditions as in Example 7, the dry coated tablet of Example 8 was obtained.

Example 9

In the same manner as in Example 7 except that the punch with which to form a plain tablet 4 had a different shape, inner core 2B having the aforementioned lattice mesh grooves 12A, 12B, 13A, 13B was obtained. The number of grooves 12A, 12B, 13A, 13B was 3 for each. The cross section of each groove was V-shaped, the opening width was set to about 0.5 mm and the depth was set to about 0.25 mm. Using the same enteric coating, the same mixed powder of outer layer 3, and the same other conditions as in Example 7, the dry coated tablet of Example 9 was obtained.

Example 10

In the same manner as in Example 7 except that the punch with which to form a plain tablet 4 had a different shape, inner core 2C having the aforementioned round grooves 14, 15 was obtained. The diameter the circle formed by the center line of each groove was set to about 4 mm. In addition, other cross section of each groove was V-shaped, the opening width was set to about 1 mm, and the depth was set to about 0.3 mm. Using the same enteric coating, the same mixed powder of outer layer 3, and the same other conditions as in Example 7, the dry coated tablet of Example 10 was obtained.

Examples 11-14

In the same manner as in Examples 7-10 except that the tableting pressure for the dry coating tableting was changed from 15 kN to 19 kN, the dry coated tablets of Examples 11-14 were obtained.

This application is based on a patent application No. 2011-262679 filed in Japan, the contents of which are incorporated in full herein.

[Explanation Of Symbols]

1: dry coated tablet, 2: inner core (enteric coating tablet containing acetylsalicylic acid), 3: outer layer, 4: plain tablet (plain tablet containing acetylsalicylic acid), 5: coating layer, 6 and 7: inner core grooves (concave parts), 8

The invention claimed is:

1. A dry coated tablet having an inner core and an outer layer, wherein the inner core is an enteric-coated tablet comprising acetylsalicylic acid, and the outer layer comprises enteric micro granules comprising a proton pump inhibitor; the enteric coating in the inner core comprises a methacrylic acid copolymer LD and an ethyl acrylate-methyl methacrylate copolymer; and a content ratio of the methacrylic acid copolymer LD and the ethyl acrylate-methyl methacrylate copolymer is 85:15 - 95:5.

2. A dry coated tablet having an inner core and an outer layer, wherein the inner core is an enteric-coated tablet comprising acetylsalicylic acid, and the outer layer comprises enteric micro granules comprising a proton pump inhibitor; and a difference in the diameter between the inner core and the dry coated tablet is not less than 2.0 mm before enteric coating of the inner core.

3. A dry coated tablet having an inner core and an outer layer, wherein the inner core is an enteric-coated tablet comprising acetylsalicylic acid, and the outer layer comprises enteric micro granules comprising a proton pump inhibitor; and a weight ratio of the inner core and the outer layer is 1:2 - 1:6.

\* \* \* \* \*